(12) United States Patent
Abreu

(10) Patent No.: US 12,076,163 B2
(45) Date of Patent: Sep. 3, 2024

(54) DEVICE CONFIGURED TO POSITION A SENSOR AT AN ABREU BRAIN THERMAL TUNNEL TERMINUS

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

( * ) Notice: Subject to any disclaimer, the term of this patent is extended or adjusted under 35 U.S.C. 154(b) by 0 days.

(21) Appl. No.: 18/156,651

(22) Filed: Jan. 19, 2023

(65) Prior Publication Data

US 2023/0157639 A1  May 25, 2023

Related U.S. Application Data

(60) Division of application No. 16/379,098, filed on Apr. 9, 2019, now Pat. No. 11,576,613, which is a continuation of application No. 15/065,292, filed on Mar. 9, 2016, now Pat. No. 10,292,655.

(60) Provisional application No. 62/131,133, filed on Mar. 10, 2015.

(51) Int. Cl.
*A61B 5/00* (2006.01)
*A61B 5/01* (2006.01)

(52) U.S. Cl.
CPC .............. *A61B 5/6835* (2013.01); *A61B 5/01* (2013.01); *A61B 5/4064* (2013.01); *A61B 5/0008* (2013.01); *A61B 5/6814* (2013.01); *A61B 5/6831* (2013.01); *A61B 2562/0271* (2013.01)

(58) Field of Classification Search
CPC ....... A61B 5/6835; A61B 5/01; A61B 5/4064; A61B 2562/0271
See application file for complete search history.

(56) References Cited

U.S. PATENT DOCUMENTS

| | | |
|---|---|---|
| 7,187,960 B2 | 3/2007 | Abreu |
| 8,834,020 B2 | 9/2014 | Abreu |
| 9,307,912 B2 | 4/2016 | Mullin |
| 9,848,815 B2 | 12/2017 | Abreu |
| 2004/0059212 A1 | 3/2004 | Abreu |
| 2010/0113894 A1 | 5/2010 | Padiy |
| 2013/0124039 A1 | 5/2013 | Abreu |
| 2013/0211772 A1 | 8/2013 | Ross, Jr. |
| 2015/0105687 A1 | 4/2015 | Abreu |
| 2015/0148628 A1 | 5/2015 | Abreu |

OTHER PUBLICATIONS

Notification of Transmittal of the International Search Report and the Written Opinion of the International Searching Authority; PCT/US2016/021513 dated May 17, 2016.
International Preliminary Report on Patentability dated Sep. 21, 2017, issued in International Application No. PCT/US2016/021513; 9pp.

*Primary Examiner* — Daniel L Cerioni
(74) *Attorney, Agent, or Firm* — Studebaker & Brackett PC

(57) ABSTRACT

Devices, apparatuses, and systems configured to assist in the location of an ABTT terminus and then to measure the temperature of the ABTT terminus.

19 Claims, 27 Drawing Sheets

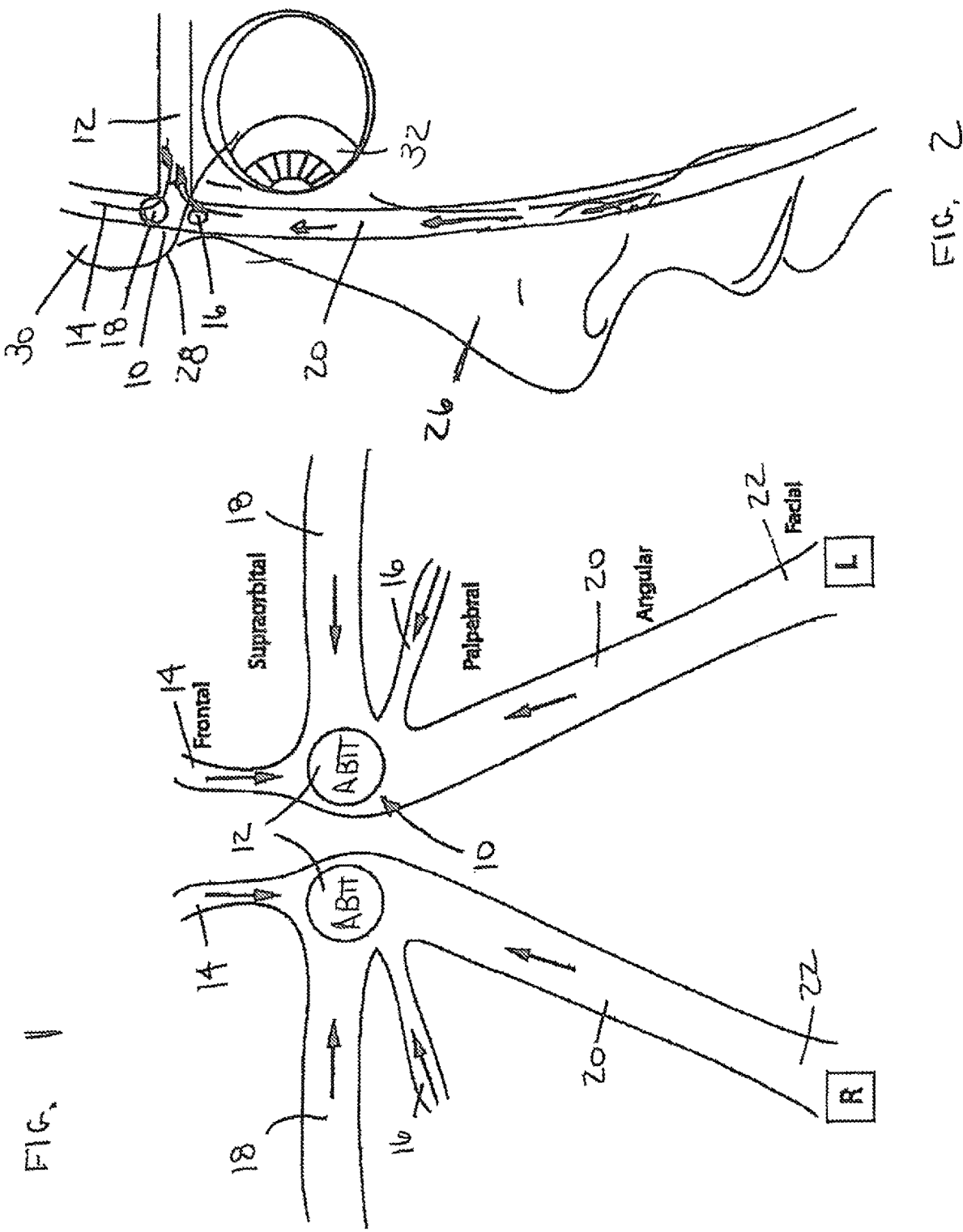

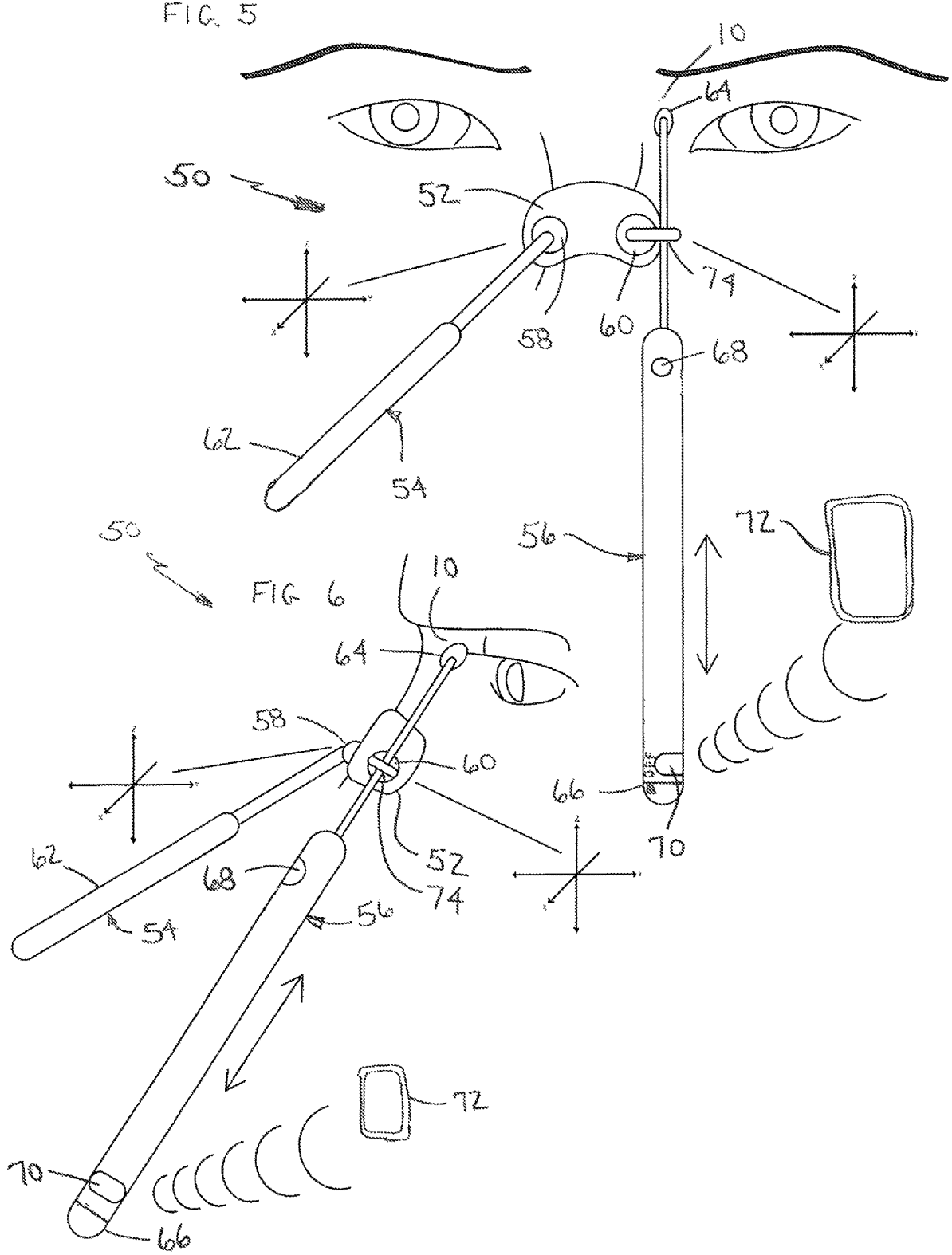

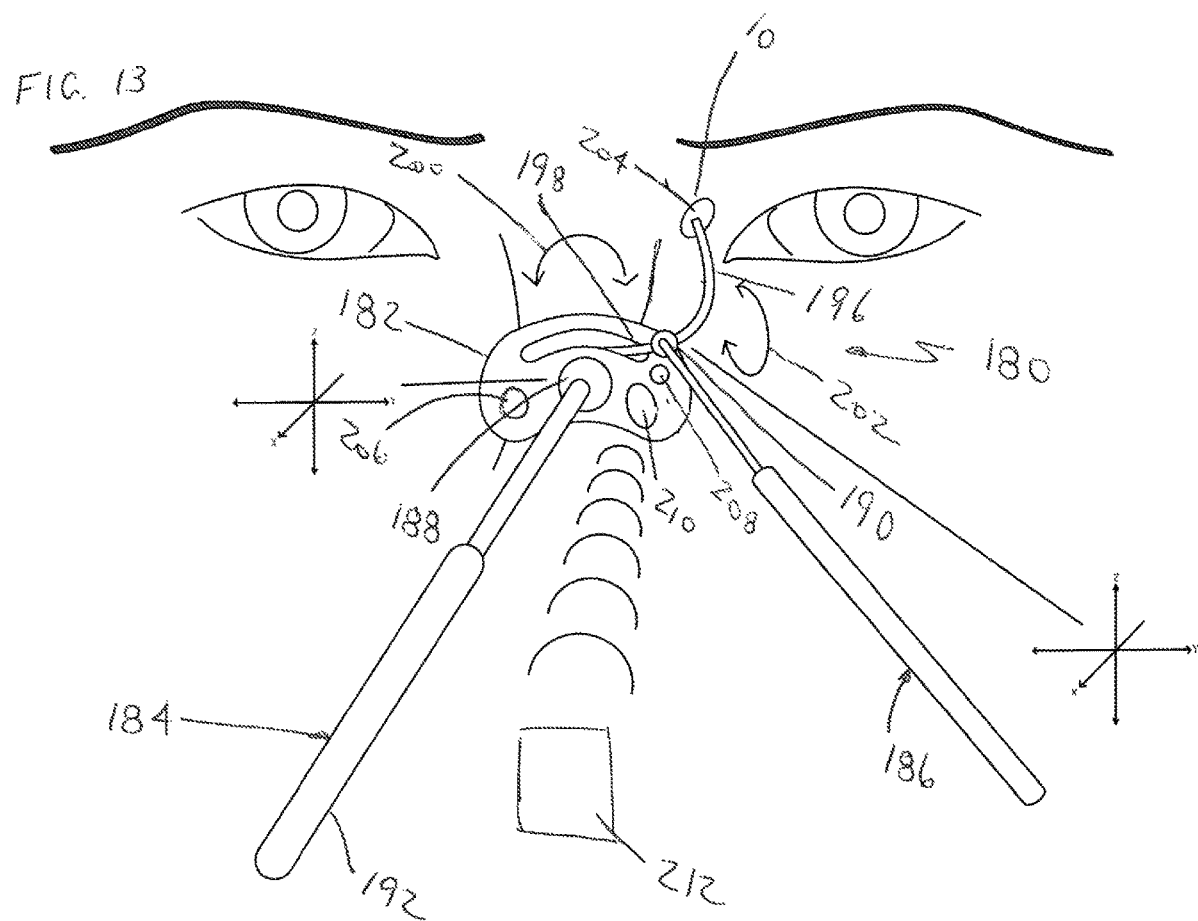
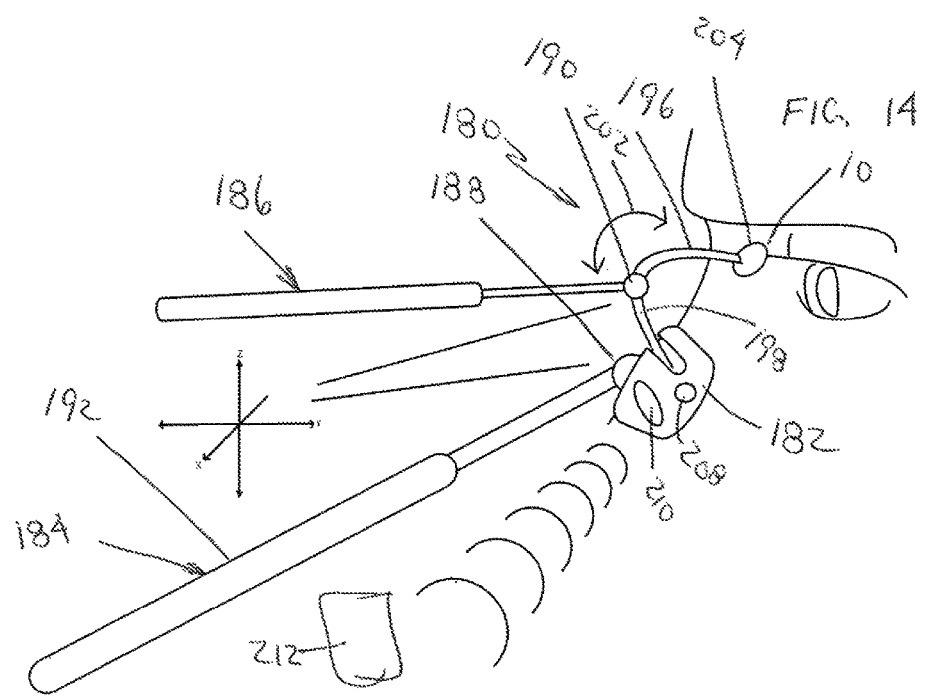

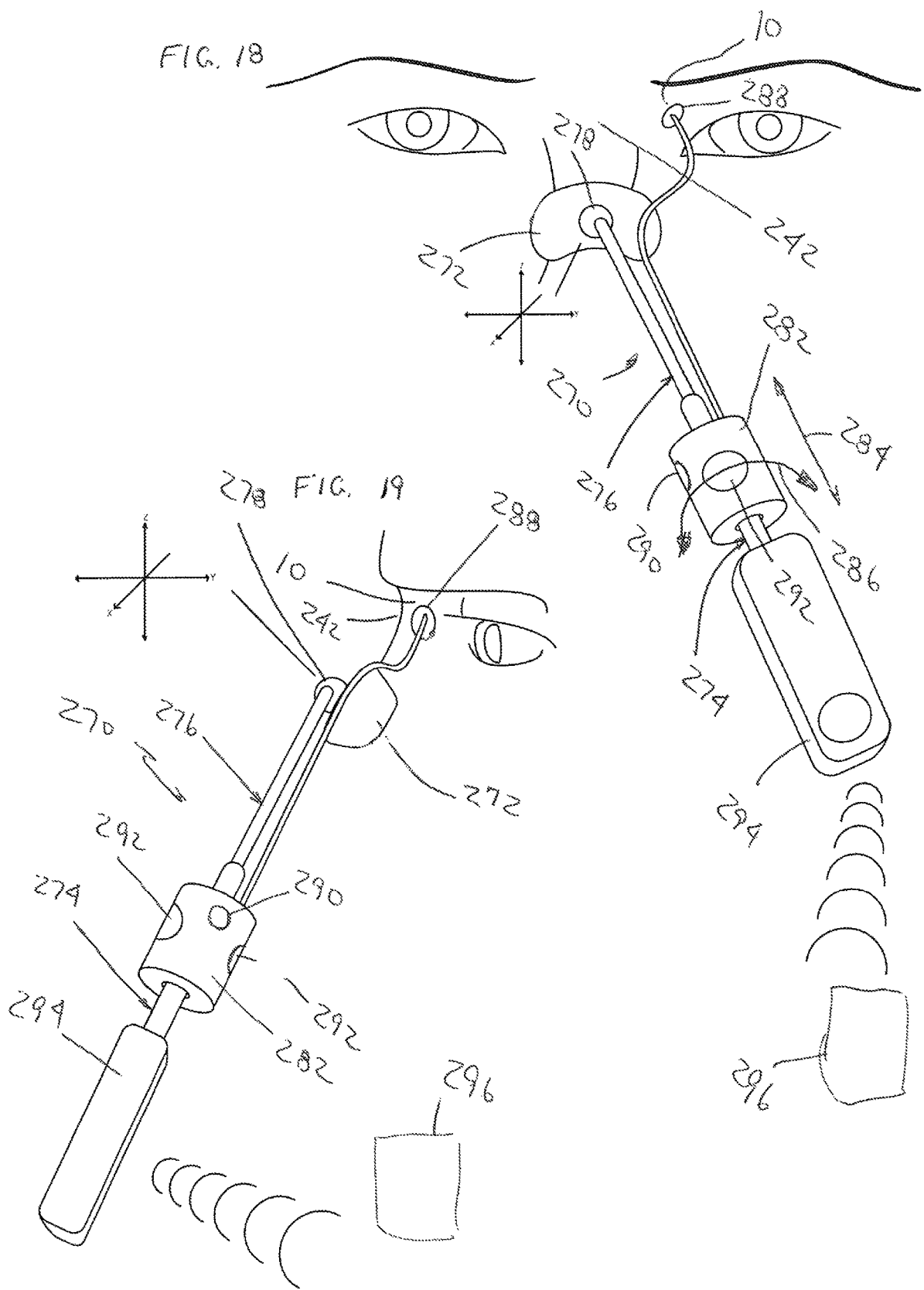

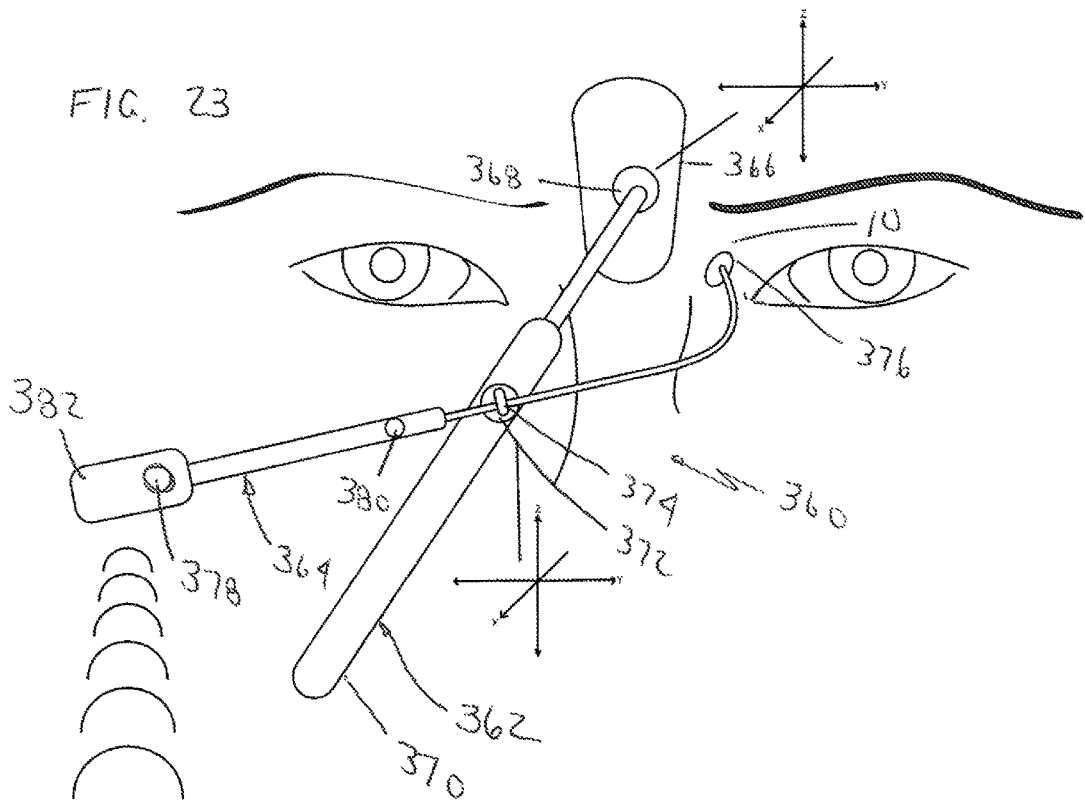
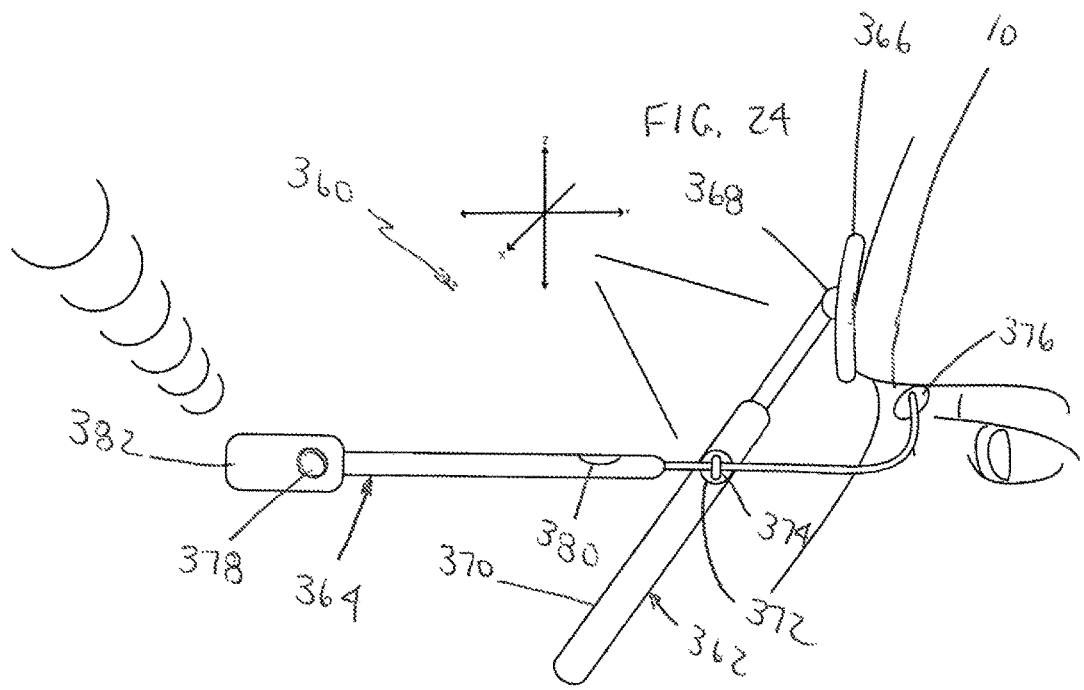

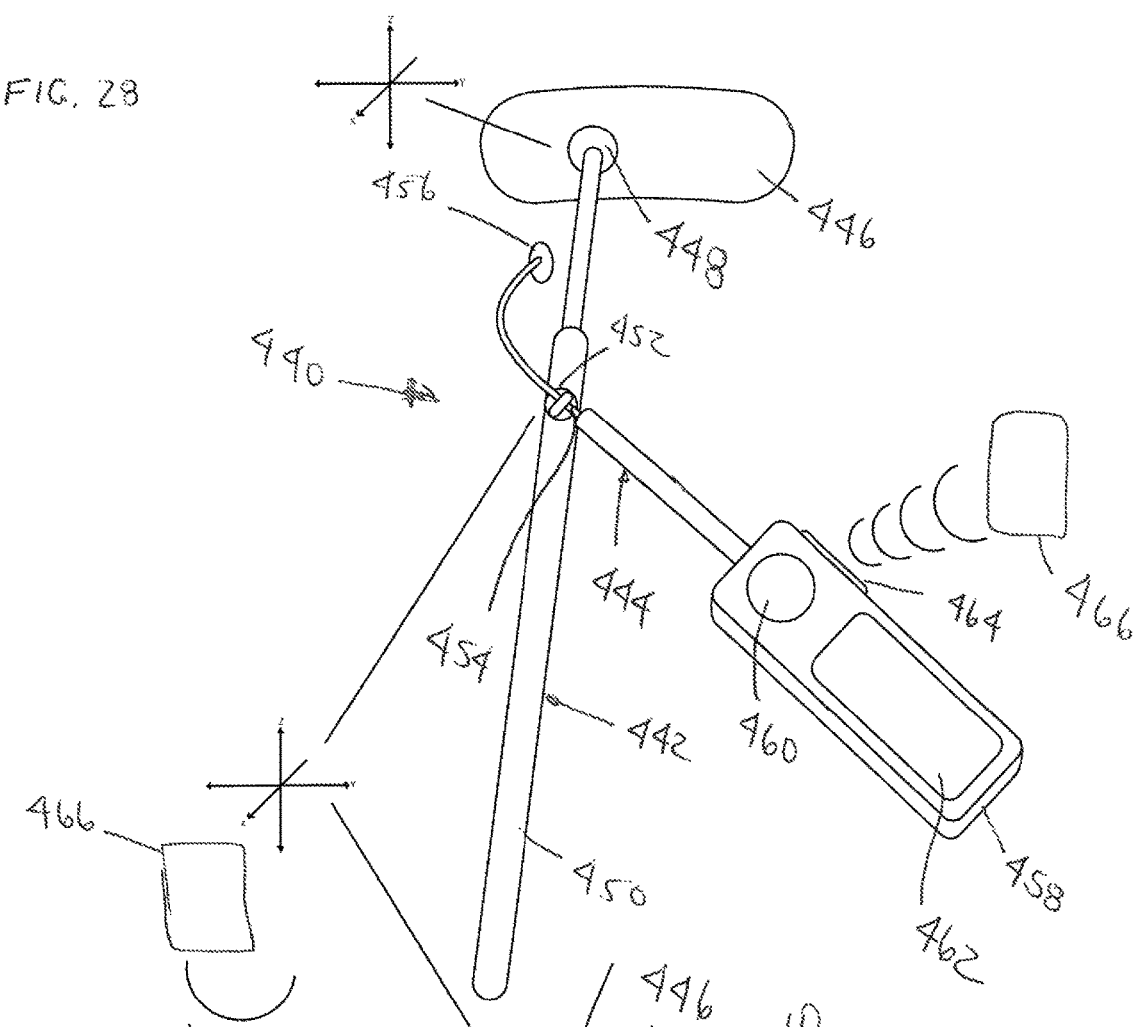
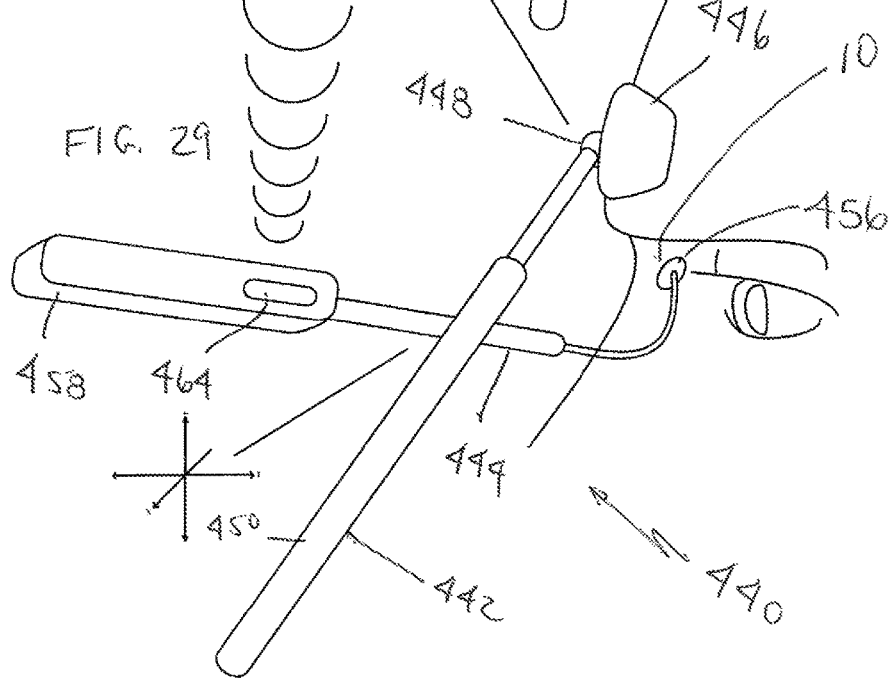

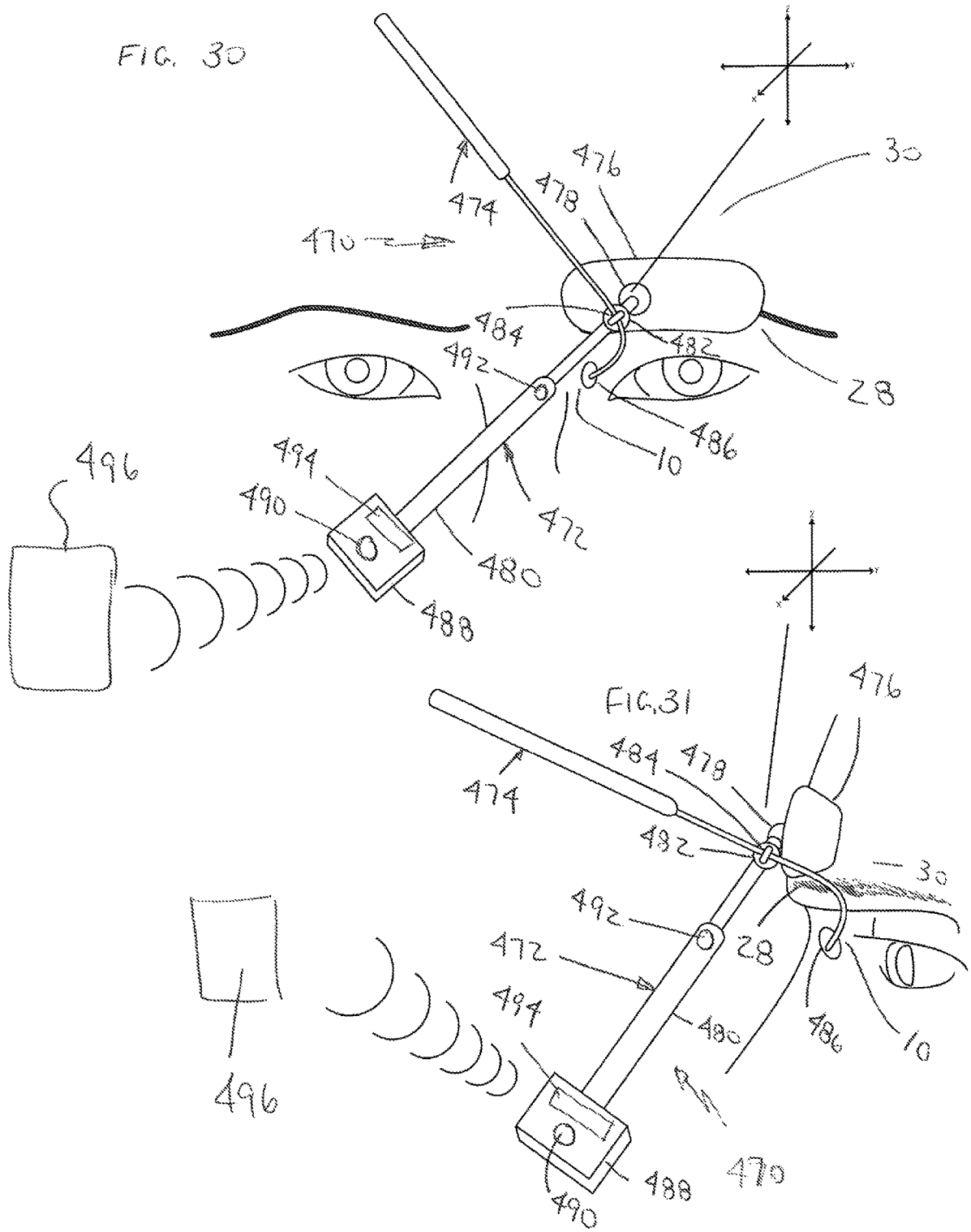

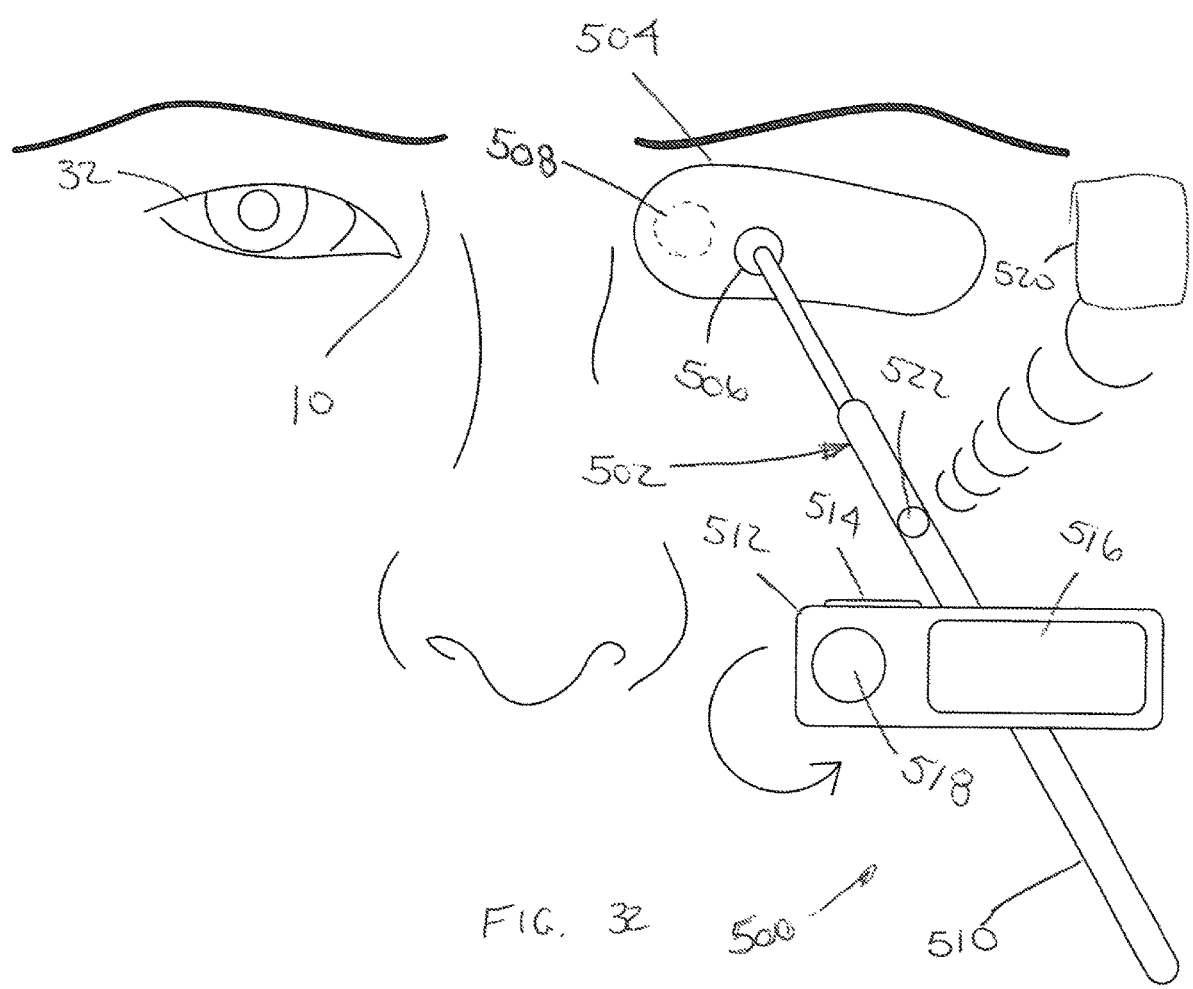

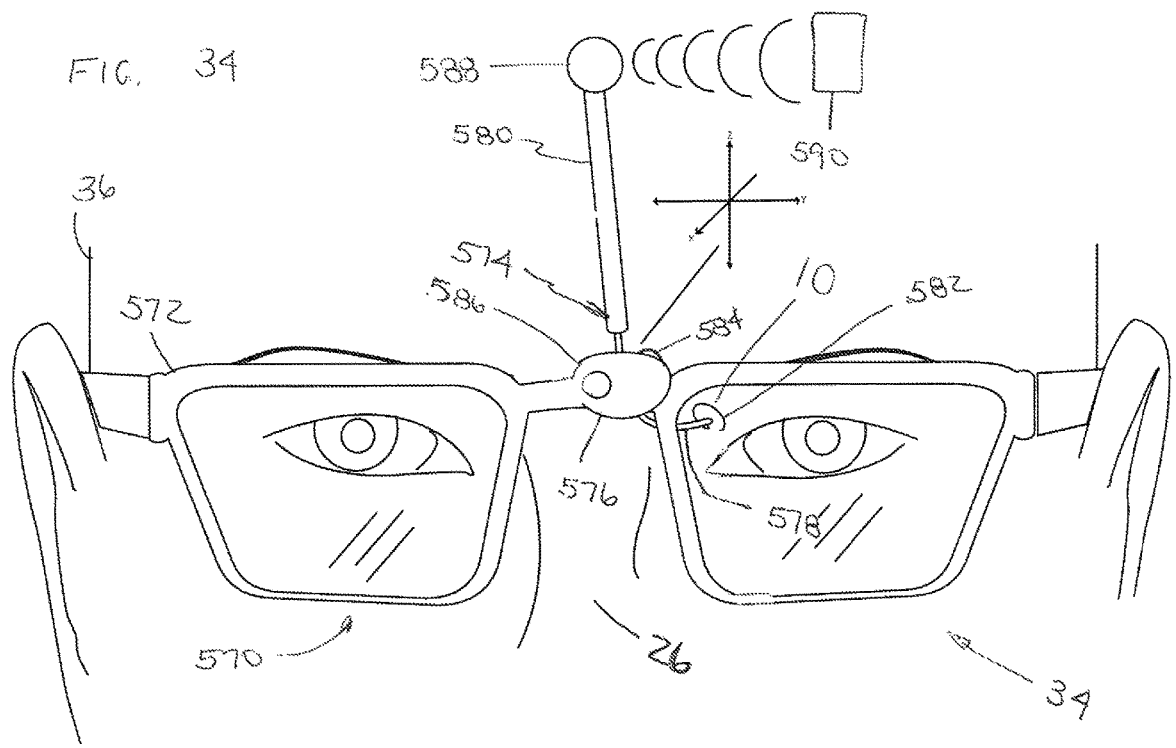
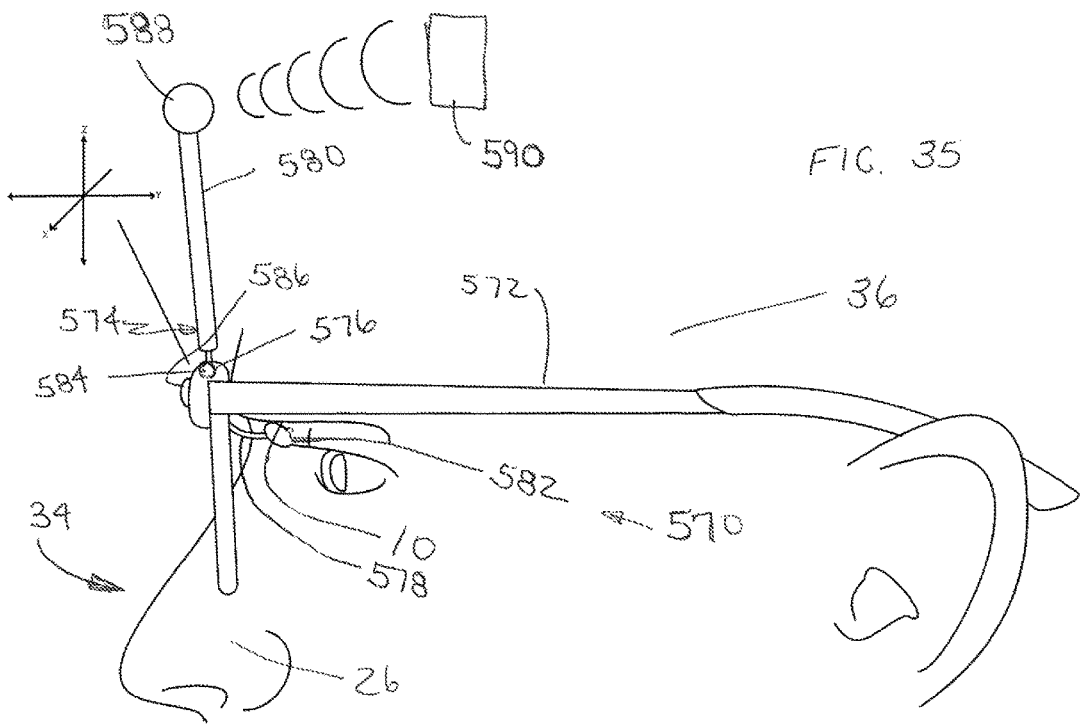

DEVICE CONFIGURED TO POSITION A SENSOR AT AN ABREU BRAIN THERMAL TUNNEL TERMINUS

CROSS-REFERENCE TO RELATED APPLICATIONS

This application is a divisional of Ser. No. 16/379,098, filed on Apr. 9, 2019, which is a continuation of U.S. patent application Ser. No. 15/065,292, filed on Mar. 9, 2016, which claims the benefit of priority to U.S. Provisional Patent Application No. 62/131,133, filed Mar. 10, 2015, which are incorporated herein by reference in their entirety.

TECHNICAL FIELD

This disclosure relates to devices configured position a sensor at an Abreu brain thermal tunnel (ABTT) terminus.

BACKGROUND

Locating the ABTT terminus and positioning a sensor on the ABTT terminus is typically performed by a person who has experience in locating the ABTT terminus, through specialized scanning procedures.

SUMMARY

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 1 is a simplified view of the Abreu brain thermal tunnel (ABTT) and facial veins associated with the ABTT.

FIG. 2 is a simplified partial cross-sectional view through a human skull in a vertical direction, showing the ABTT and certain other facial features.

FIG. 5 is a closer view of the first device of FIG. 4.

FIG. 6 is a side view of the first device of FIGS. 4 and 5.

FIG. 13 is a closer view of the fifth device of FIG. 12.

FIG. 14 is a side view of the fifth device of FIGS. 12 and 13.

FIG. 18 is a closer view of the eighth device of FIG. 17.

FIG. 19 is a side view of the eighth device of FIGS. 17 and 18.

FIG. 23 is a closer view of the eleventh device of FIG. 22.

FIG. 24 is a side view of the eleventh device of FIGS. 22 and 23.

FIG. 28 is a closer view of the fourteenth device of FIG. 27.

FIG. 29 is a side view of the fourteenth device of FIGS. 27 and 28.

FIG. 30 is a view of a fifteenth device in accordance with an exemplary embodiment of the present disclosure.

FIG. 31 is a side view of the fifteenth device of FIG. 30.

FIG. 32 is a view of a sixteenth device in accordance with an exemplary embodiment of the present disclosure.

FIG. 34 is a view of an eighteenth device in accordance with an exemplary embodiment of the present disclosure.

FIG. 35 is a side view of the eighteenth device of FIG. 34.

DETAILED DESCRIPTION

Figure 3:
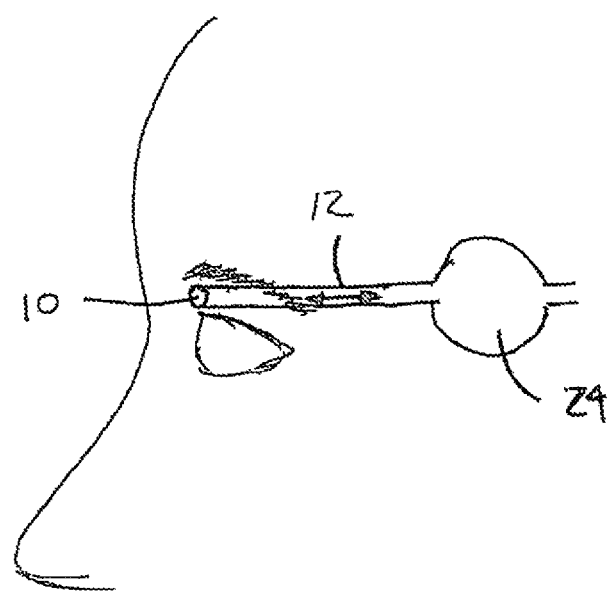
FIG. 3 is a stylized representation of a flow of blood into a brain core.

The present disclosure arises from the discovery that an Abreu brain thermal tunnel, or ABTT, provides the first known means of vascular communication directly with the center of the brain. Anatomically and physiologically speaking, and as shown in FIGS. 1-3, ABTT 12 includes a continuous, direct, and undisturbed connection between a brain core 24 at the control center of the brain and an ABTT terminus 10. The physical and physiological events at one end of the tunnel are reproduced at the opposite end. ABTT 12 enables the direct communication of thermal energy between ABTT terminus 10 and brain core 24 without significant barriers. Accordingly, the present disclosure describes devices, mechanisms, apparatuses, and systems that are configured to aid in positioning a sensor on ABTT terminus 10 by positioning a sensor in an area of a face that is close to the ABTT such that an operator can then manipulate the devices, mechanisms, apparatuses, and systems to position the sensor on ABTT terminus 10, after which the sensor receives signals from ABTT terminus 10; e.g., thermal or temperature signals.

Applicant has disclosed devices, mechanisms, apparatuses, and systems for the measurement of temperature at ABTT terminus 10 in co-pending U.S. patent application Ser. Nos. 14/512,421, 14/593,848, 14/594,122, and 14/603,353, incorporated herein by reference in their entirety. The present devices, mechanisms, apparatuses, and systems described herein provide additional features and advantages, as will be understood by a person of skill in the art from reading the present description.

The facial end of ABTT 12 is adjacent to a small region of skin without subcutaneous fat, the exterior surface of which is described herein as ABTT target area or ABTT terminus 10. For simplicity, ABTT terminus 10 can also be described as skin that is on, over, or adjacent to ABTT 12, and which measures about 11 mm in diameter measured from the medial corner of an eye 32 at the medial canthal tendon and extends superiorly for about 6 mm, and then extends into the upper eyelid in a horn-like projection for another 22 mm.

Anatomy shows the convergence of four veins at ABTT target area 10: frontal 14, superior palpebral 16, supraorbital 18, and angular 20. As angular vein 20 extends further from ABTT 12, it transitions into facial vein 22. Having converged, the blood from these veins flows toward brain core 24 from ABTT target area 10 near the canthal corner of eye 32 into the center of the brain, which is the temperature center or thermal storage area of the body. FIGS. 1 and 2 show the approximate location of these veins in relation to other facial features. Angular/facial vein 20/22 runs up alongside a nose 26, superior palpebral vein 16 runs along an eyebrow 28, and frontal vein 14 and supraorbital vein 18 run through a forehead 30.

As described herein, veins 14, 16, 18, 20, and 22 converge in the medial canthal area between the corner of eye 32 and the bridge of nose 26 and connect directly, without inhibition, to the center of the brain, i.e., brain core 24. These vessels lack valves, which are typically an important barrier to measurement of temperature in a core location of the brain in the hypothalamic region of the brain. The hypothalamic region of the brain is the link between the central nervous system and the endocrine system and, as such, acts as the center of control for many basic bodily functions such as, for example, hunger, thirst, body temperature, fatigue, blood pressure, immune responses, circadian cycles, hormone production, hormone secretion, and many other bodily functions.

It should be understood that throughout this disclosure, the terms apparatus, device, and mechanism can be used interchangeably to refer to at least portions of the various embodiments. Because some embodiments are configured to include a plurality of elements working together, these embodiments can be described as systems.

Figure 4:
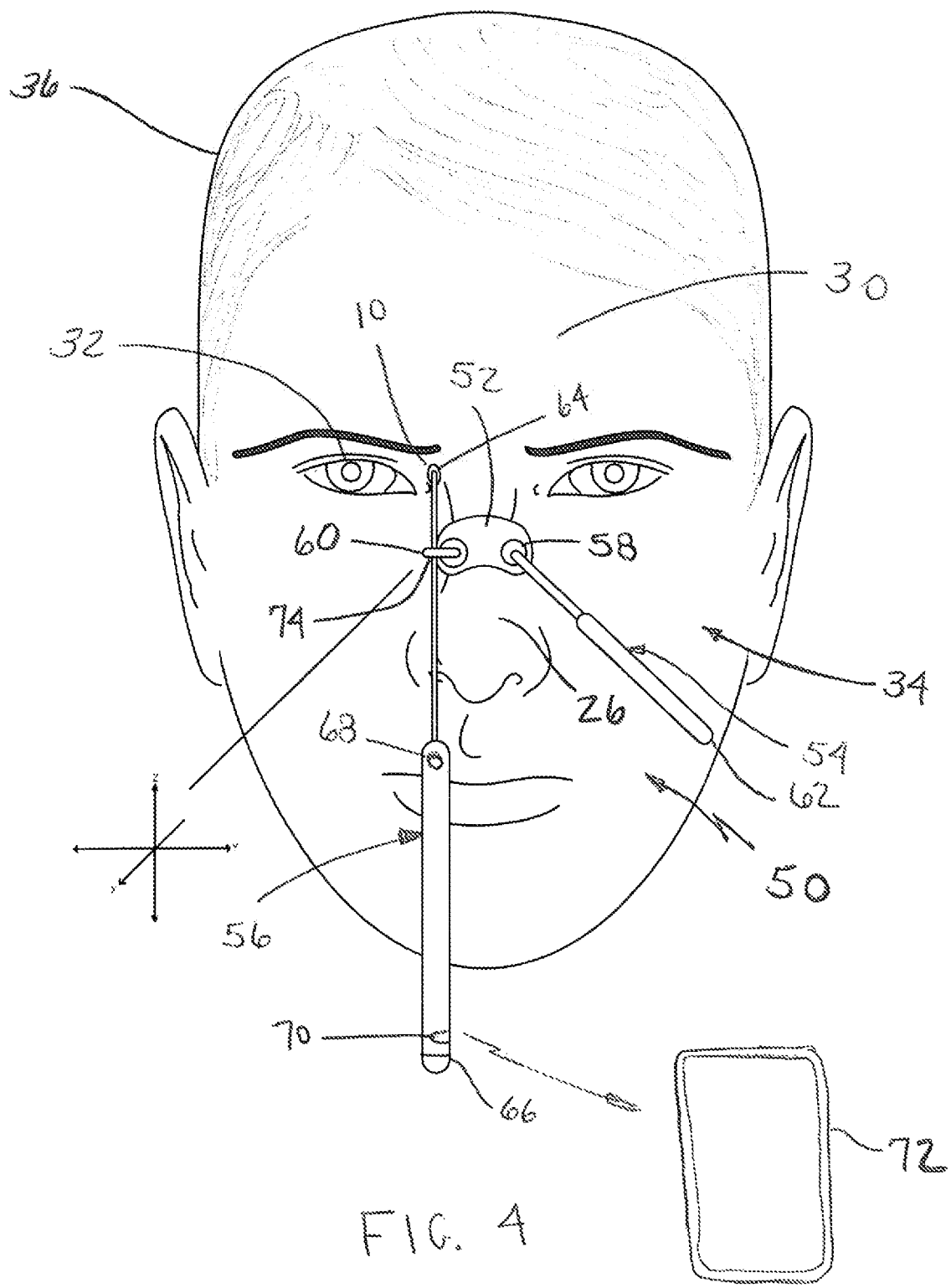
FIG. 4 is a view of a first device in accordance with an exemplary embodiment of the present disclosure.

FIGS. 4-6 show a first device in accordance with an exemplary embodiment of the present disclosure, indicated generally at 50. Device 50 is configured to be supported on nose 26 of a face 34 of a subject or patient 36. As should be understood from the following description, device 50 is configured to be held in place by a user while the user positions a sensor on ABTT terminus 10.

Device 50 is configured to include a face or nose support 52, a support arm 54, and a temperature sensor support 56, which includes a handle. Nose support 52 is configured to include a first connection 58, which is configured to attach or connect support arm 54 to nose support 52, and a second connection 60, which is configured to attach or connect temperature sensor support 56 to nose support 52. Nose support 52 can be configured to be formed of a semi-rigid or rigid material. In addition, nose support 52 can be configured to include a pad (not shown) to provide cushioning and compliance with nose 26. Nose support 52 can be shaped in an arc that approximately matches the curvature of nose 26.

Support arm 54 can be configured to be rigidly attached to nose support 52 by first connection 58. Alternatively, first connection 58 can be configured to swivel or pivot to permit a user to position support arm 54 in an orientation that assists the user in keeping nose support 52 securely in contact with nose 26 by the force of pressure on nose support 52 applied through support arm 54. Support arm 54 is configured to include a handle 62 sized and dimensioned to permit a user to hold support arm 54 securely and to apply pressure on nose support 52.

Most face supports disclosed herein require application of form onto the face support to secure the face support in position on the face. It should be observed that in some cases an adhesive, typically a relatively weak adhesive, can be used to assist maintaining the position of the face support on the face. In some cases, the skin of the face may need to be prepared before use of a face support such as by washing the face to remove oils and dirt, which decreases the risk of the face support sliding during application of force and pressure on the face through the face support.

Temperature sensor support 56 is configured to include a temperature sensor 64, which is sized and dimensioned to interface with ABTT terminus 10 and which can be configured to include a convex surface to match the concave geometry of ABTT terminus 10. Temperature sensor support 56 is further configured to include a switch 66 configured to control the on and off operation of device 50, a light or other indicator 68 configured to indicate or provide feedback when a user locates ABTT terminus 10, and can be configured to include a transmitter 70 to transmit temperature signals to a separate electronic device 72, which can be, for example, a laptop, cell phone, tablet, or other electronic device configured to receive the transmitted temperature signals. It should be understood that transmitter 70, and other transmitters described in this disclosure, can be transceivers configured to transmit and receive signals.

Second connection 60 is configured to include an eyelet 74, which is configured to slidably or movably support temperature sensor support 56 to permit a user to adjust the position of temperature sensor support 56, such that the user is able to position temperature sensor 64 on ABTT terminus 10. As a user moves temperature sensor 64 in the area of ABTT terminus 10, temperature sensor 64 is transmitting or sending temperature signals to a processor (not shown) that can be located in temperature sensor support 56. When device 50, or a processor thereof, determines that a peak temperature has been found that exceeds a predetermined temperature, which is an indication of the location of ABTT terminus 10, then indicator 68 can be actuated to provide notice that the location of ABTT terminus 10 has been found to a user or operator. The temperature signals from temperature sensor 64 can be transmitted continuously or in a burst by transmitter 70 to separate electronic device 72 for further processing, storage, or notification of another person remotely.

Figure 7:
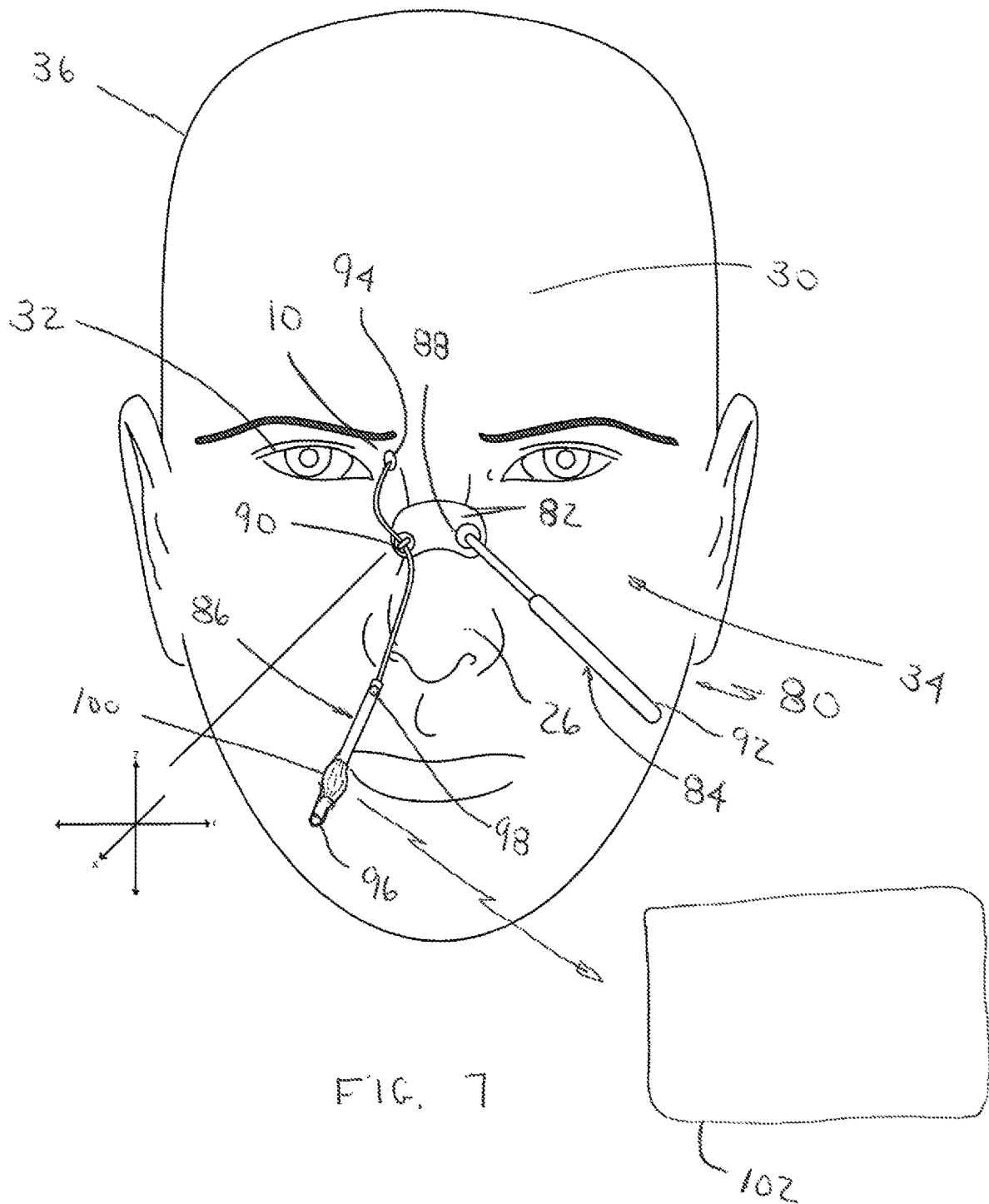
FIG. 7 is a view of a second device in accordance with an exemplary embodiment of the present disclosure.

FIG. 7 shows a second device in accordance with an exemplary embodiment of the present disclosure, indicated generally at 80. Device 80 is configured to be supported on nose 26 of face 34 of subject or patient 36. As should be understood from the following description, device 80 is configured to be held in place by a user while the user positions a sensor on ABTT terminus 10.

Device 80 is configured to include a face or nose support 82, a support arm 84, and a temperature sensor support 86. Nose support 82 is configured to include a first connection 88, which is configured to attach or connect support arm 84 to nose support 82, and a second connection 90, which is configured to attach or connect temperature sensor support 86 to nose support 82. Nose support 82 can be configured to be formed of a semi-rigid or rigid material. In addition, nose support 82 can be configured to include a pad (not shown) to provide cushioning and compliance with nose 26. Nose support 82 can be shaped in an arc that approximately matches the curvature of nose 26.

Support arm 84 can be configured to be rigidly attached to nose support 82 by first connection 88. Alternatively, first connection 88 can be configured to swivel or pivot to permit a user to position support arm 84 in an orientation that assists the user in keeping nose support 82 securely in contact with nose 26. Support arm 84 is configured to include a handle 92 sized and dimensioned to permit a user to hold support arm 84 securely.

Temperature sensor support 86 is configured to include a temperature sensor 94, which is sized and dimensioned to interface with ABTT terminus 10, and which can be configured to include a convex surface to match the concave geometry of ABTT terminus 10. Temperature sensor support 86 is further configured to include a switch 96 to control the on and off operation of device 80, and a light or other indicator 98 configured to indicate when a user locates ABTT terminus 10, and can be configured to include a transmitter 100 to transmit temperature signals to a separate electronic device 102, which can be, for example, a laptop, cell phone, tablet, or other electronic device configured to receive the transmitted temperature signals.

Second connection 90 is configured to slidably or movably support temperature sensor support 86 to permit a user to move temperature sensor support 86 such that the user is able to position temperature sensor 94 on ABTT terminus 10. As the user moves temperature sensor 94 in the area of ABTT terminus 10, temperature sensor 94 is transmitting or sending temperature signals to a processor (not shown) that can be located in temperature sensor support 86. When device 80, or a processor thereof, determines that a peak temperature has been found that exceeds a predetermined temperature, which is an indication of the location of ABTT terminus 10, then indicator 98 can be actuated to provide notice to a user or operator. The temperature signals from temperature sensor 94 can be transmitted continuously or in a burst by transmitter 100 to separate electronic device 102 for further processing, storage, or notification of another person remotely.

Figure 8:
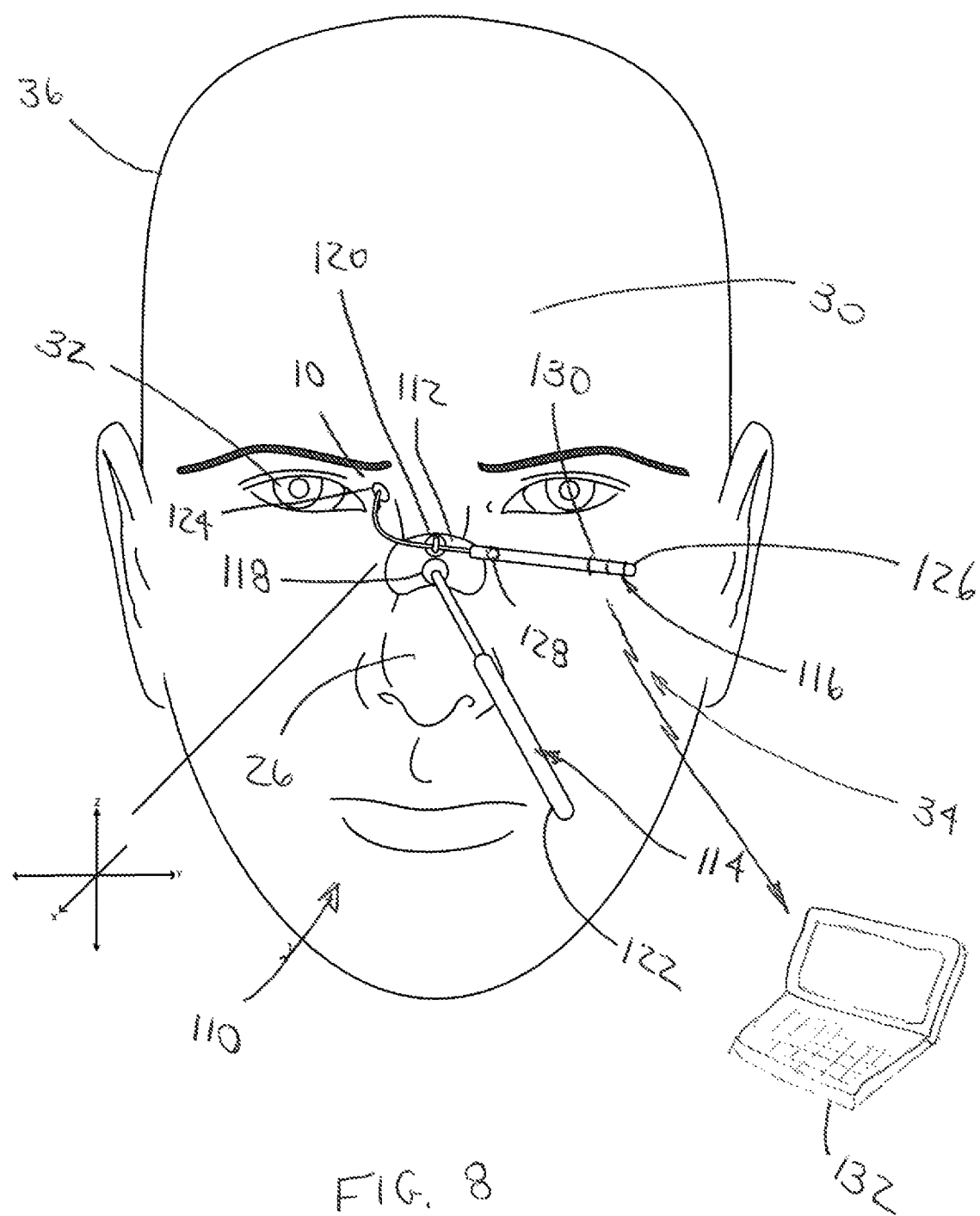
FIG. 8 is a view of a third device in accordance with an exemplary embodiment of the present disclosure.

FIG. 8 shows a third device in accordance with an exemplary embodiment of the present disclosure, indicated generally at 110. Device 110 is configured to be supported on nose 26 of face 34 of subject or patient 36. As should be understood from the following description, device 110 is configured to be held in place by a user while the user positions a temperature sensor on ABTT terminus 10.

Device 110 is configured to include a face or nose support 112, a support arm 114, and a temperature sensor support 116. Nose support 112 is configured to include a first connection 118, which is configured to attach or connect support arm 114 to nose support 112, and a second connection 120, which is configured to attach or connect temperature sensor support 116 to nose support 112. Nose support 112 can be configured to be formed of a semi-rigid or rigid material. In addition, nose support 112 can be configured to include a pad (not shown) to provide cushioning and compliance with nose 26. Nose support 112 can be shaped in an arc that approximately matches the curvature of nose 26.

Support arm 114 can be configured to be rigidly attached to nose support 112 by first connection 118. Alternatively, first connection 118 can be configured to swivel or pivot to permit a user to position support arm 114 in an orientation that assists the user in keeping nose support 112 securely in contact with nose 26. Support arm 114 is configured to include a handle 122 sized and dimensioned to permit a user to hold support arm 114 securely.

Temperature sensor support 116 is configured to include a temperature sensor 124, which is sized and dimensioned to interface with ABTT terminus 10, and which can be configured to include a convex surface to match the concave geometry of ABTT terminus 10. Temperature sensor support 116 is further configured to include a switch 126 to control the on and off operation of device 110, a light or other indicator 128 configured to indicate when a user locates ABTT terminus 10, and can be configured to include a transmitter 130 to transmit temperature signals to a separate electronic device 132, which can be, for example, a laptop, cell phone, tablet, or other electronic device configured to receive the transmitted temperature signals.

Second connection 120 is configured to slidably or movably support temperature sensor support 116 to permit the user to move temperature sensor support 116 such that the user is able to position temperature sensor 124 on ABTT terminus 10. As the user moves temperature sensor 124 in the area of ABTT terminus 10, temperature sensor 124 is transmitting or sending temperature signals to a processor (not shown) that can be located in temperature sensor support 116. When the processor of device 110 determines that a peak temperature has been found that exceeds a predetermined temperature, which is an indication of the location of ABTT terminus 10, then indicator 128 can be actuated to provide notice to a user or operator. The temperature signals from temperature sensor 124 can be transmitted continuously or in a burst by transmitter 130 to separate electronic device 132 for further processing, storage, or notification of another person remotely.

Figure 9:
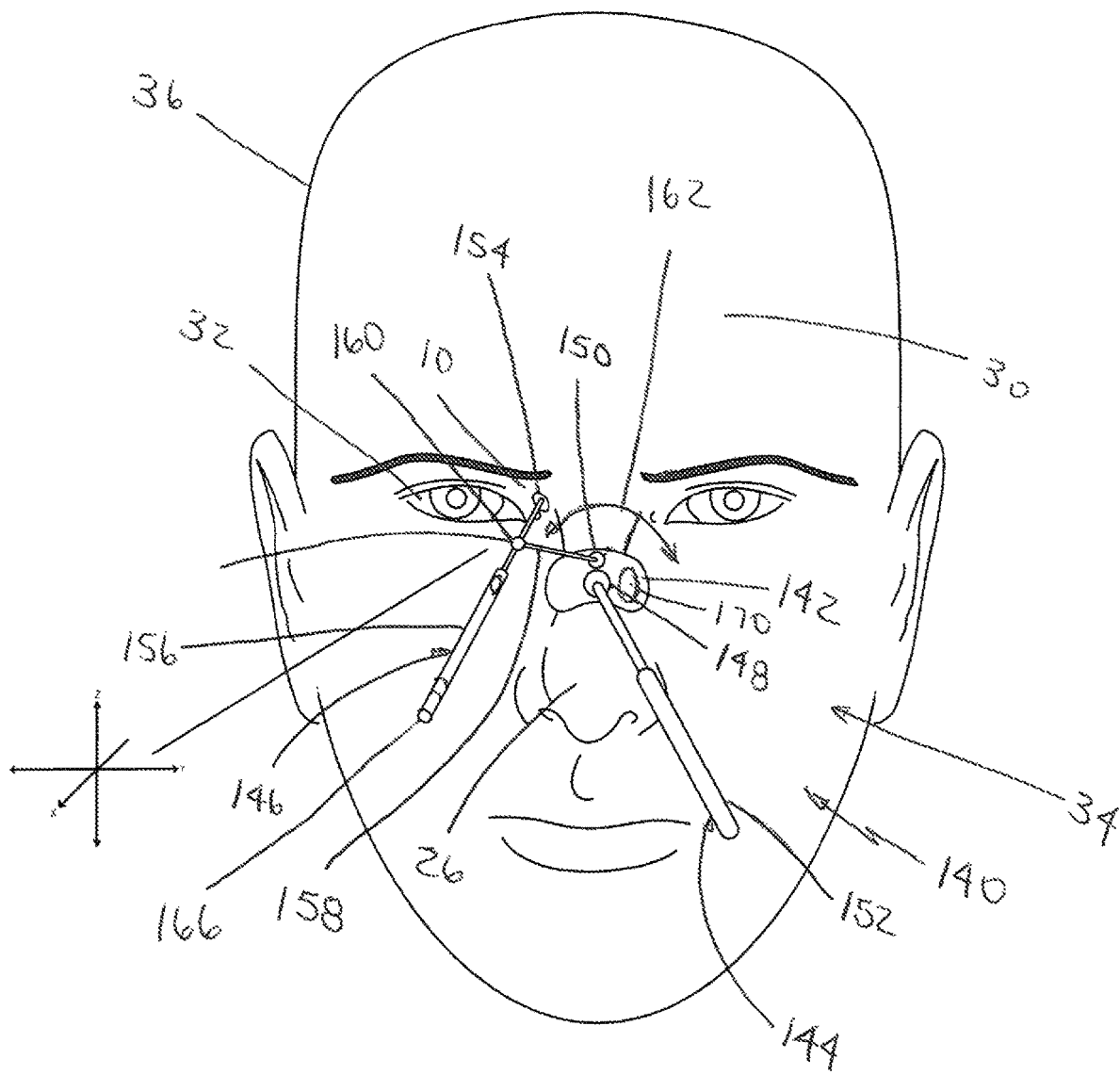
FIG. 9 is a view of a fourth device in accordance with an exemplary embodiment of the present disclosure.
Figure 10:
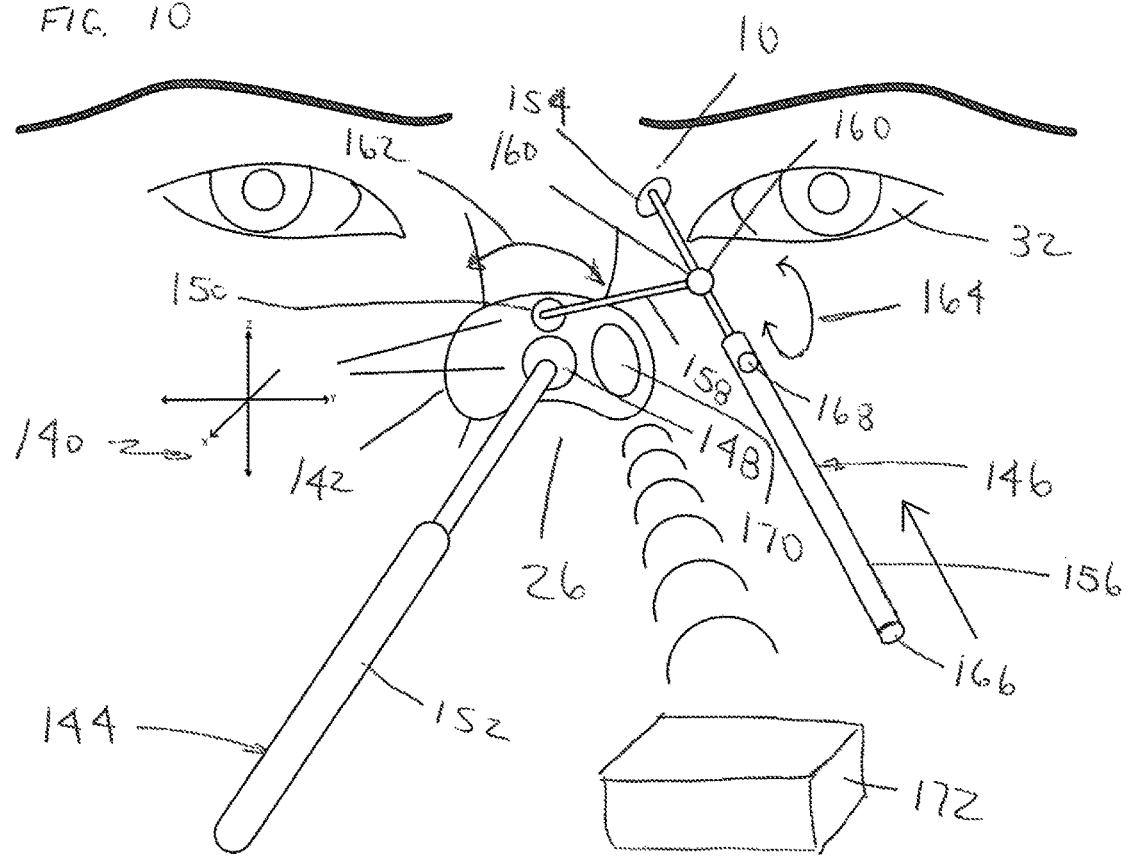
FIG. 10 is a closer view of the fourth device of FIG. 9.
Figure 11:
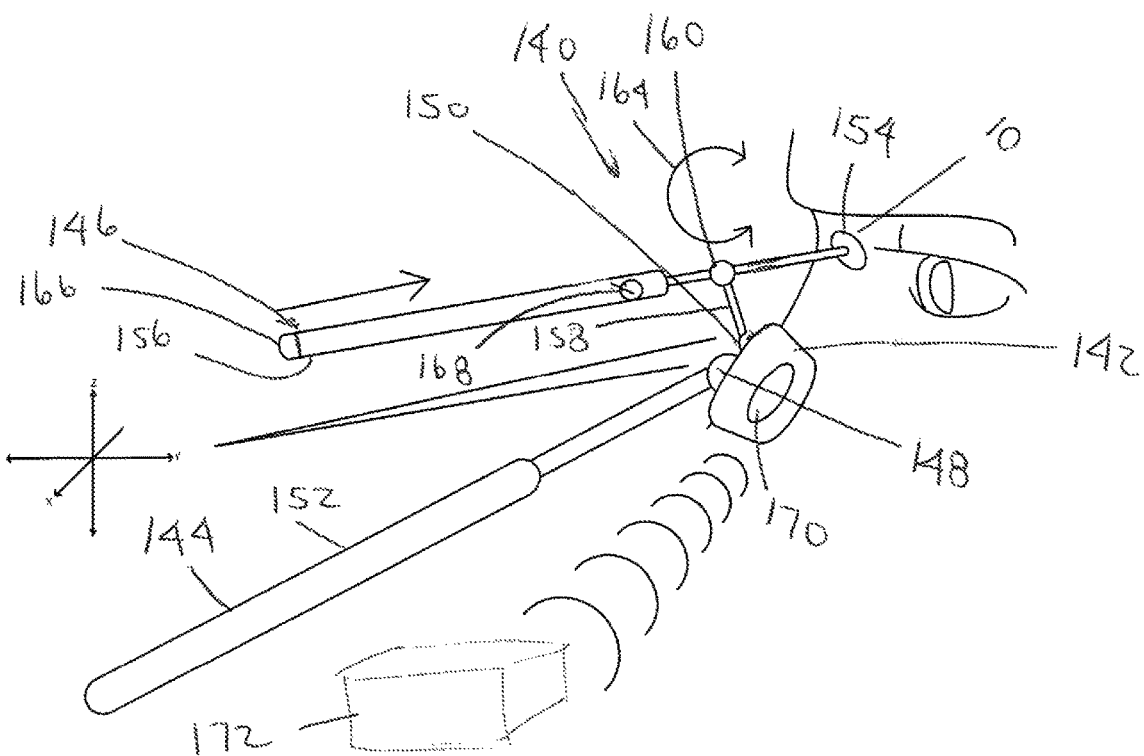
FIG. 11 is a side view of the fourth device of FIGS. 9 and 10.

FIGS. 9-11 show a fourth device in accordance with an exemplary embodiment of the present disclosure, indicated generally at 140. Device 140 is configured to be supported on nose 26 of face 34 of subject or patient 36. As should be understood from the following description, device 140 is configured to be held in place by a user while the user positions a sensor on ABTT terminus 10.

Device 140 is configured to include a face or nose support 142, a support arm 144, and a temperature sensor support 146. Nose support 142 is configured to include a first connection 148, which is configured to attach or connect support arm 144 to nose support 142, and a second connection 150, which is configured to attach or connect temperature sensor support 146 to nose support 142. Nose support 142 can be configured to be formed of a semi-rigid or rigid material. In addition, nose support 142 can be configured to include a pad (not shown) to provide cushioning and compliance with nose 26. Nose support 142 can be shaped in an arc that approximately matches the curvature of nose 26.

Support arm 144 can be configured to be rigidly attached to nose support 142 by first connection 148. Alternatively, first connection 148 can be configured to swivel or pivot to permit a user to position support arm 144 in an orientation that assists the user in keeping nose support 142 securely in contact with nose 26. Support arm 144 is configured to include a handle 152 sized and dimensioned to permit a user to hold support arm 144 securely.

Temperature sensor support 146 is further configured to include a sensor arm 156 and a support connecting arm 158. Support connecting arm 158 is positioned between sensor arm 156 and nose support 142 and is connected to sensor arm 156 by a sensor arm pivot 160 and is connected to nose support 142 by second connection 150. Second connection 150 is configured to allow support connecting arm 158 to rotate in a first arc 162 that permits a user to move temperature sensor support 146 to measure the temperature of left ABTT terminus 10 and right ABTT terminus 10, in addition to permitting adjustment of the position of temperature sensor support 146. Sensor arm pivot 160 is configured to allow sensor arm 156 to rotate in a second arc 164 that is at an angle with respect to first arc 162. Functionally, second connection 150 is configured to enable side-to-side or horizontal adjustment, and sensor arm pivot 160 is configured to enable vertical adjustment. Both adjustments are configured to enable a user to position a sensor on ABTT terminus 10, or to move the temperature sensor from left ABTT terminus 10 to right ABTT terminus 10 or vice versa.

Temperature sensor support 146 is configured to include a temperature sensor 154, which is sized and dimensioned to interface with ABTT terminus 10, and which can be configured to include a convex surface to match the concave geometry of ABTT terminus 10. Temperature sensor support 146 is further configured to include a switch 166 to control the on and off operation of device 140, and a light or other indicator 168 configured to indicate when a user locates ABTT terminus 10, and can be configured to include a transmitter 170 to transmit temperature signals to a separate electronic device 172, which can be, for example, a laptop, cell phone, tablet, or other electronic device configured to receive the transmitted temperature signals. In the exemplary embodiment of FIGS. 10 and 11, separate electronic device 172 is shown as an entertainment console, such as a video game console.

As noted herein, second connection 150 and sensor arm pivot 160 are configured to movably support temperature sensor support 156 to permit a user to move temperature sensor support 156 such that temperature sensor 154 is positionable by a user on ABTT terminus 10. As the user moves temperature sensor 154 in the area of ABTT terminus 10, temperature sensor 154 is transmitting or sending temperature signals to a processor that can be located in temperature sensor support 146 or in nose support 142. When the processor of device 140 determines that a peak temperature has been found that exceeds a predetermined temperature, which is an indication of the location of ABTT terminus 10, then indicator 168 can be actuated to provide notice to a user or operator. The temperature signals from temperature sensor 154 can be transmitted continuously or in a burst by transmitter 170 to separate electronic device 172 for further processing, storage, or notification of another person remotely.

Figure 12:
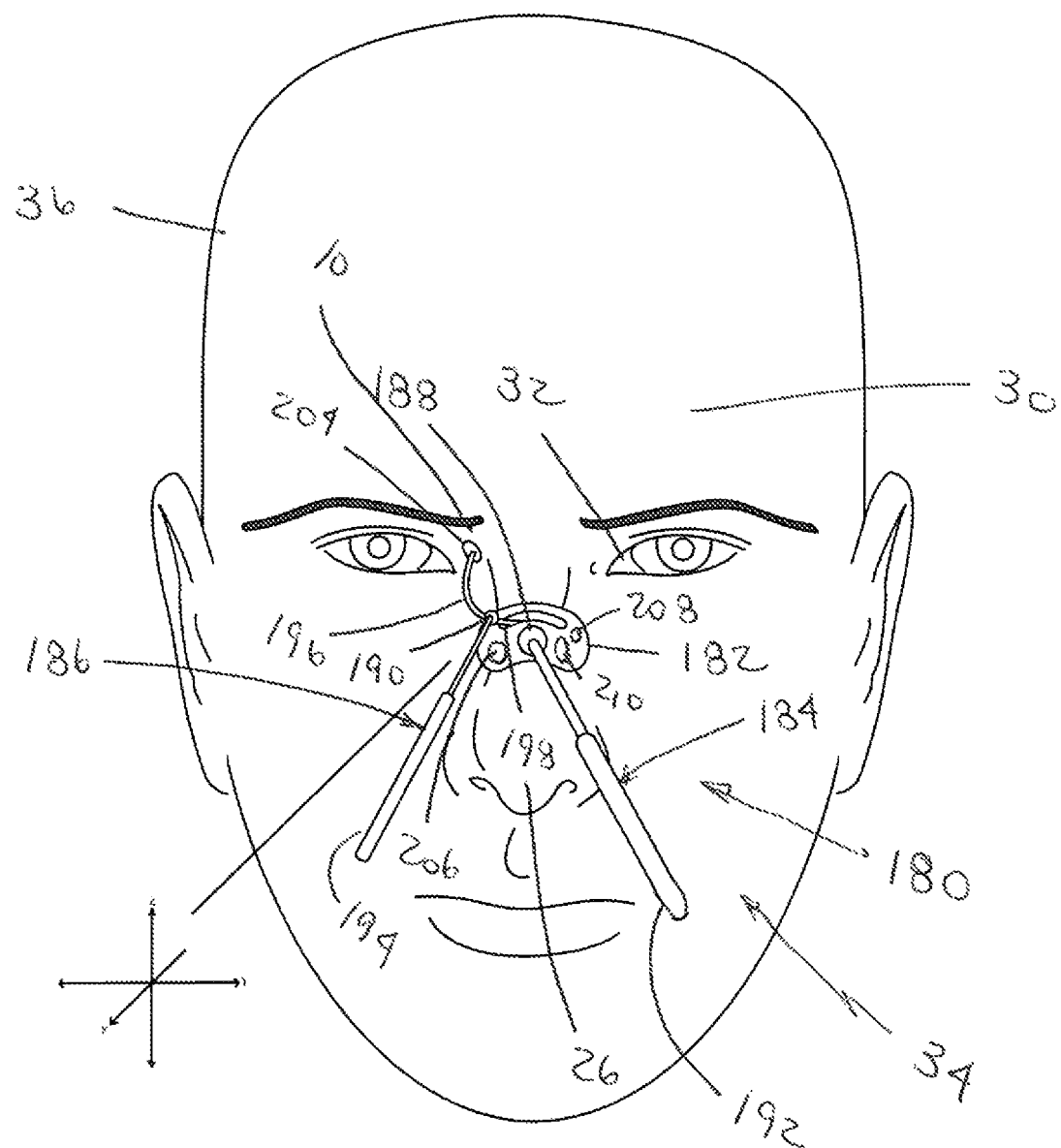
FIG. 12 is a view of a fifth device in accordance with an exemplary embodiment of the present disclosure.

FIGS. 12-14 show a fifth device in accordance with an exemplary embodiment of the present disclosure, indicated generally at 180. Device 180 is configured to be supported on nose 26 of face 34 of subject or patient 36. As should be understood from the following description, device 180 is configured to be held in place by a user while the user positions a sensor on ABTT terminus 10.

Device 180 is configured to include a face or nose support 182, a support arm 184, and a temperature sensor support 186. Nose support 182 is configured to include a connection 188, which is configured to attach or connect support arm 184 and temperature sensor support 186 to nose support 182. Nose support 182 can be configured to be formed of a semi-rigid or rigid material. In addition, nose support 182 can be configured to include a pad (not shown) to provide cushioning and compliance with nose 26. Nose support 182 can be shaped in an arc that approximately matches the curvature of nose 26.

Support arm 184 can be configured to be rigidly attached to nose support 182 by connection 188. Alternatively, connection 188 can be configured to swivel or pivot to permit a user to position support arm 184 in an orientation that assists the user in keeping nose support 182 securely in contact with nose 26. Support arm 184 is configured to include a handle 192 sized and dimensioned to permit a user to hold support arm 184 securely.

Temperature sensor support 186 is further configured to include a sensor handle 194, a sensor arm 196 connected or attached to sensor handle 194 at an angle to sensor handle 194, and a swing arm 198 that is rotatably positioned on the pivot that is coaxial with connection 188. Sensor handle 194 and sensor arm 196 are connected to swing arm 198 by a sensor pivot 190. Connection 188 is configured to allow swing arm 198 to rotate in a first arc 200 that permits a user to move temperature sensor support 186 to measure left ABTT terminus 10 and right ABTT terminus 10, in addition to permitting adjustment of the position of temperature sensor support 186. Sensor pivot 190 is configured to allow sensor arm 196 to rotate in a second arc 202 that is at an angle with respect to first arc 200. Functionally, sensor arm 196 is configured and connected to enable side-to-side or horizontal adjustment, and sensor pivot 190 is configured and connected to enable vertical adjustment. Both adjustments can enable a user to position a sensor on ABTT terminus 10, or to move the sensor from left ABTT terminus 10 to right ABTT terminus 10 or vice versa.

Temperature sensor support 186 is configured to include a temperature sensor 204, which is sized and dimensioned to interface with ABTT terminus 10, and which can be configured to include a convex surface to match the concave geometry of ABTT terminus 10. Nose support 182 is further configured to include a switch 206 to control the on and off operation of device 180, and a light or other indicator 208 configured to indicate when a user locates ABTT terminus 10, and can be configured to include a transmitter 210 to transmit temperature signals to a separate electronic device 212, which can be, for example, a laptop, cell phone, tablet, or other electronic device configured to receive the transmitted temperature signals.

As noted herein, swing arm 198 and sensor pivot 190 are configured to support temperature sensor support 186 to enable a user to move temperature sensor support 186 to position temperature sensor 204 on ABTT terminus 10. As a user is moving temperature sensor 204 in the area of ABTT terminus 10, temperature sensor 204 is transmitting or sending temperature signals to a processor (not shown) that can be located in temperature sensor support 186 or in nose support 182. When the processor of device 180 determines that a peak temperature has been found that exceeds a predetermined temperature, which is an indication of the location of ABTT terminus 10, then indicator 208 can be actuated to provide notice to a user or operator. The temperature signals from temperature sensor 204 can be transmitted continuously or in a burst by transmitter 210 to separate electronic device 212 for further processing, storage, or notification of another person remotely.

Figure 15:
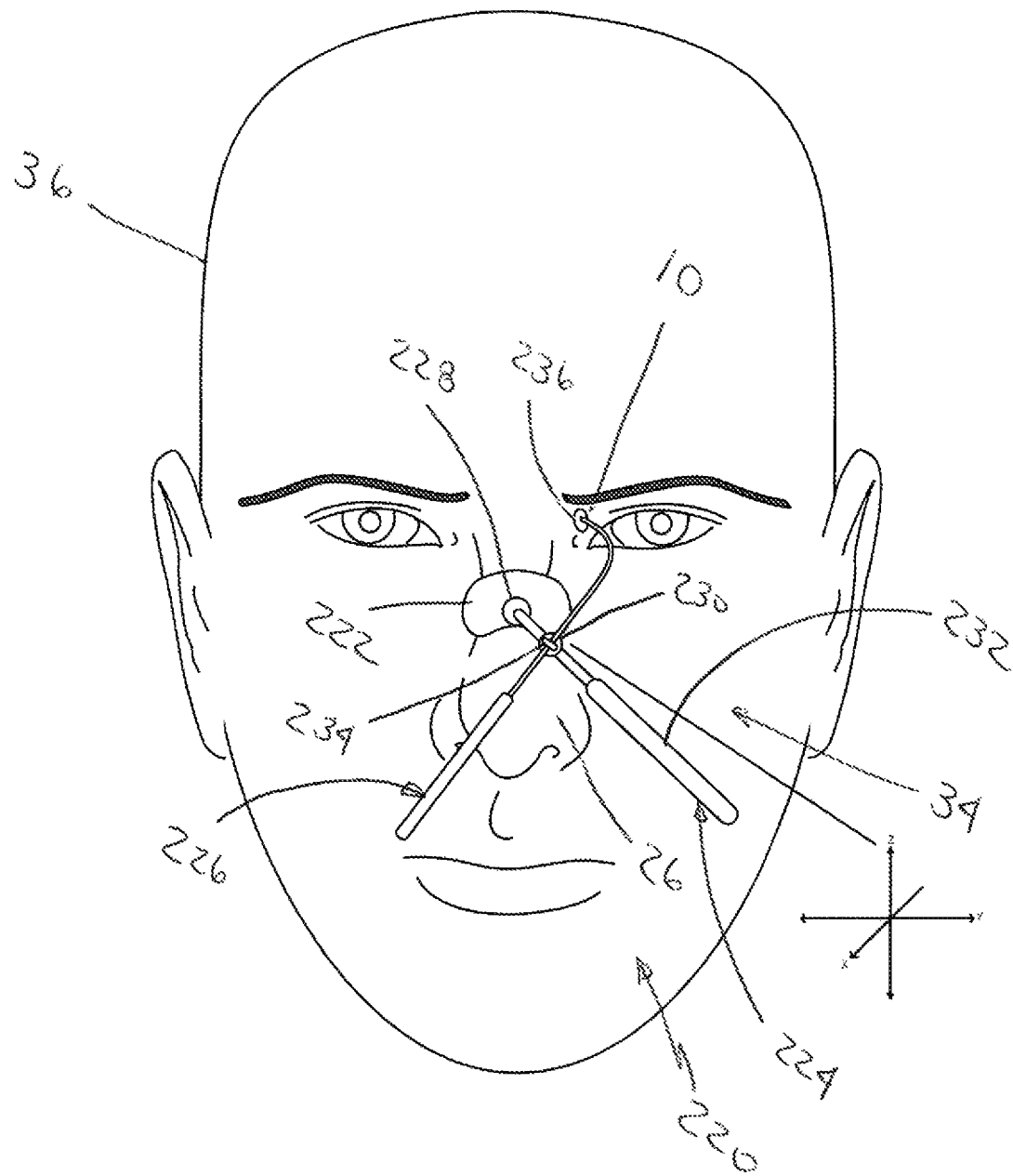
FIG. 15 is a view of a sixth device in accordance with an exemplary embodiment of the present disclosure.

FIG. 15 shows a sixth device in accordance with an exemplary embodiment of the present disclosure, indicated generally at 220. Device 220 is configured to be supported on nose 26 of face 34 of subject or patient 36. As should be understood from the following description, device 220 is configured to be held in place by a user while the user positions a sensor on ABTT terminus 10.

Device 220 is configured to include a face or nose support 222, a support arm 224, and a temperature sensor support 226. Nose support 222 is configured to include a connection 228, which is configured to attach or connect support arm 224 to nose support 222. Nose support 222 can be configured to be formed of a semi-rigid or rigid material. In addition, nose support 222 can be configured to include a pad (not shown) to provide cushioning and compliance with nose 26. Nose support 222 can be shaped in an arc that approximately matches the curvature of nose 26.

Support arm 224 can be configured to be rigidly attached to nose support 222 by connection 228. Alternatively, connection 228 can be configured to swivel or pivot to permit a user to position support arm 224 in an orientation that assists the user in keeping nose support 222 securely in contact with nose 26. Support arm 224 is configured to include a handle 232 sized and dimensioned to permit a user to hold support arm 224 securely. Temperature sensor support 226 is connected to support arm 224 by a pivot 230, which is also configured to permit temperature sensor support 226 to move longitudinally through an eyelet 234 located in pivot 230.

Temperature sensor support 226 is configured to include a temperature sensor 236, which is sized and dimensioned to interface with ABTT terminus 10, and which can be configured to include a convex surface to match the concave geometry of ABTT terminus 10. Device 220 can be configured with the features of other embodiments disclosed herein, such as a switch to turn device 220 on and off, an indicator, and a transmitter, though such are not specifically indicated in this embodiment.

Pivot 230 is configured to both slidably and movably support temperature sensor support 226 to permit a user to move temperature sensor support 226 such that the user is able to position temperature sensor 234 on ABTT terminus 10, which can be located by the user as described herein.

Figure 16:
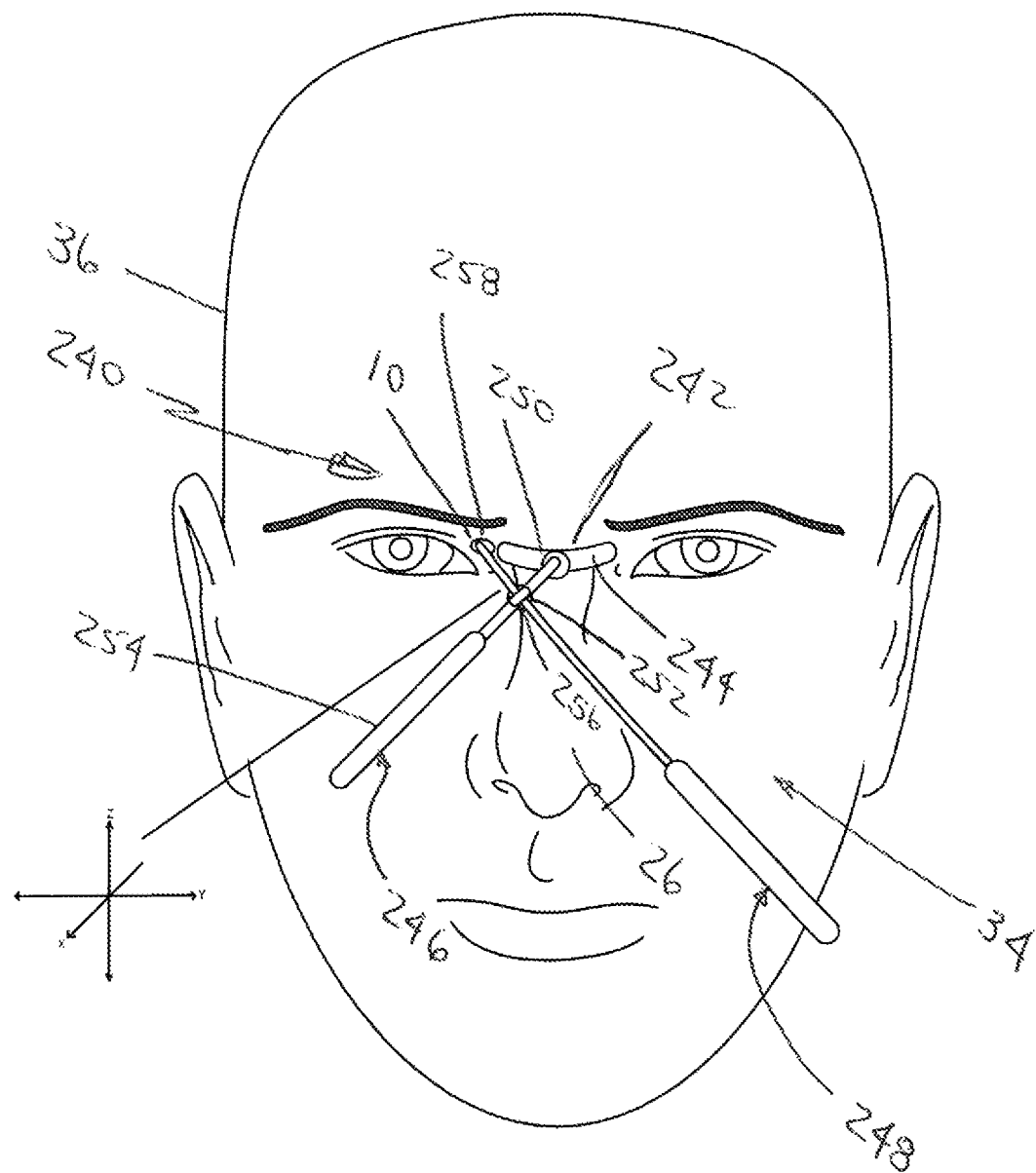
FIG. 16 is a view of a seventh device in accordance with an exemplary embodiment of the present disclosure.

FIG. 16 shows a seventh device in accordance with an exemplary embodiment of the present disclosure, indicated generally at 240. Device 240 is configured to be supported on a bridge 242 of nose 26 of face 34 of subject or patient 36. As should be understood from the following description, device 240 is configured to be held in place by a user while the user positions a sensor on ABTT terminus 10.

Device 240 is configured to include a face or nose bridge support 242, a support arm 246, and a temperature sensor support 248. Nose bridge support 242 is configured to include a connection 250, which is configured to attach or connect support arm 246 to nose bridge support 244. Nose bridge support 244 can be configured to be formed of a semi-rigid or rigid material. In addition, nose bridge support 244 can be configured to include a pad (not shown) to provide cushioning and compliance with nose 26. Nose bridge support 244 can be shaped in an arc that approximately matches the curvature of bridge 242.

Support arm 246 can be configured to be rigidly attached to nose bridge support 244 by connection 250. Alternatively, connection 250 can be configured to swivel or pivot to permit a user to position support arm 246 in an orientation that assists the user in keeping nose bridge support 244 securely in contact with nose 26. Support arm 246 is configured to include a handle 254 sized and dimensioned to permit a user to hold support arm 246 securely. Temperature sensor support 248 is connected to support arm 246 by a pivot 252, which is also configured to permit temperature sensor support 248 to move longitudinally through an eyelet 256 located in pivot 252.

Temperature sensor support 248 is configured to include a temperature sensor 258, which is sized and dimensioned to interface with ABTT terminus 10, and which can be configured to include a convex surface to match the concave geometry of ABTT terminus 10. Device 240 can be configured with the features of other embodiments disclosed herein, such as a switch to turn device 240 on and off, an indicator, and a transmitter, though such are not specifically indicated in this embodiment.

Pivot 252 is configured to both slidably and movably support temperature sensor support 248 to permit a user to move temperature sensor support 248 such that temperature sensor 258 is positionable on ABTT terminus 10, which can be located by the user as described herein.

Figure 17:
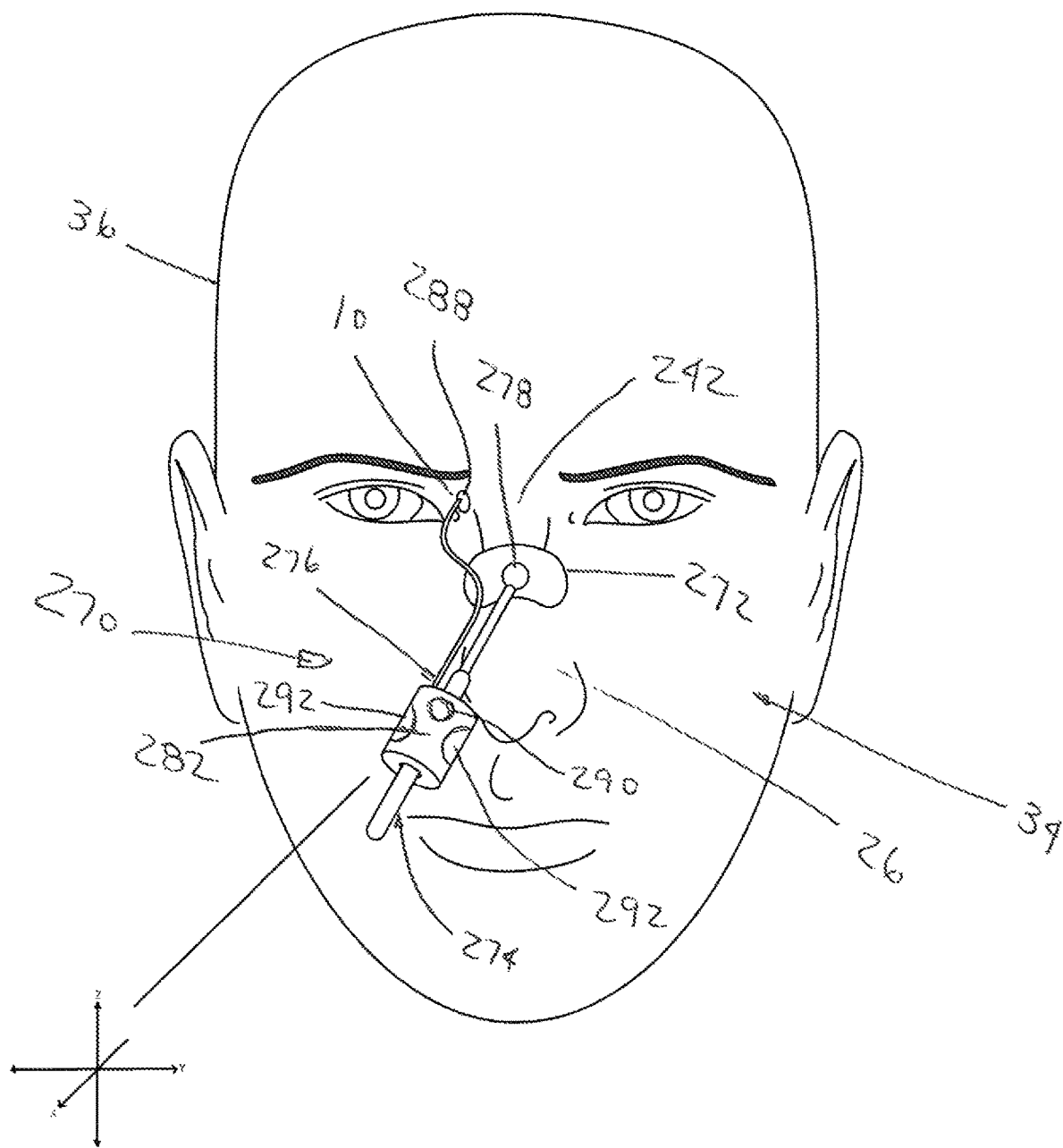
FIG. 17 is a view of an eighth device in accordance with an exemplary embodiment of the present disclosure.

FIGS. 17-19 show an eighth device in accordance with an exemplary embodiment of the present disclosure, indicated generally at 270. Device 270 is configured to be supported on nose 26 or bridge 242 of face 34 of subject or patient 36. As should be understood from the following description, device 270 is configured to be held in place by a user while the user positions a sensor on ABTT terminus 10.

Device 270 is configured to include a face or nose support 272, a support arm 274, and a temperature sensor support 276. Nose support 272 is configured to include a connection 278, which is configured to attach or connect support arm 274 to nose support 272. Nose support 272 can be configured to be formed of a semi-rigid or rigid material. In addition, nose support 272 can be configured to include a pad (not shown) to provide cushioning and compliance with nose 26. Nose support 272 can be shaped in an arc that approximately matches the curvature of nose 26.

Support arm 274 can be configured to be rigidly attached to nose support 272 by connection 278. Alternatively, connection 278 can be configured to swivel or pivot to permit a user to position support arm 274 in an orientation that assists the user in keeping nose support 272 securely in contact with nose 26. Temperature sensor support 276 includes a support body 282 rotatably and slidably positioned on support arm 274, which thus permits temperature sensor support to move longitudinally in a longitudinal direction 284 and rotatably in an arc 286 about temperature sensor support 276. Thus, the interface of support body 282 with support arm 284 provides a user with the ability to adjust the position of a temperature sensor 288, positioned on temperature sensor support 248, to interface with ABTT terminus 10. It should be understood that the movement of support body 282 can be manual or automatic. If the movement is automatic, such movement is guided by readings from temperature sensor 288. Temperature sensor 258 is sized and dimensioned to interface with ABTT terminus 10, and which can be configured to include a convex surface to match the concave geometry of ABTT terminus 10.

Nose support 272 is further configured to include a switch 290 to control the on and off operation of device 270, a light or other indicator 292 configured to indicate when a user locates ABTT terminus 10, and can be configured to include a transmitter 294 to transmit temperature signals to a separate electronic device 296, which can be, for example, a laptop, cell phone, tablet, or other electronic device configured to receive the transmitted temperature signals.

Figure 20:
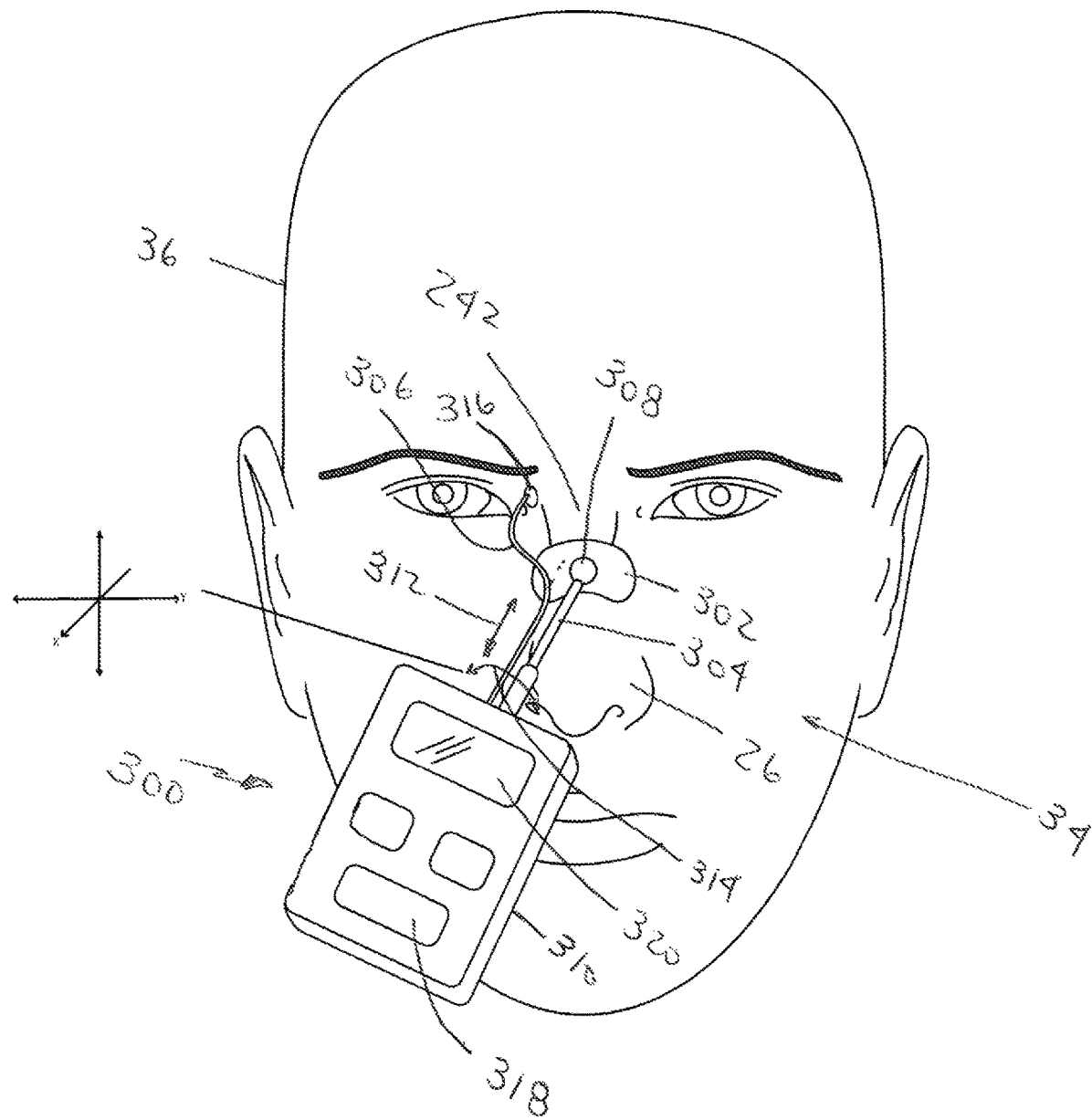
FIG. 20 is a view of a ninth device in accordance with an exemplary embodiment of the present disclosure.

FIG. 20 shows a ninth device in accordance with an exemplary embodiment of the present disclosure, indicated generally at 300. Device 300 is configured to be supported on nose 26 or bridge 242 of face 34 of subject or patient 36. As should be understood from the following description, device 300 is configured to be held in place while a temperature sensor is positionable on ABTT terminus 10.

Device 300 is configured to include a face or nose support 302, a support arm 304, a temperature sensor support 306, and a controller unit 310. Nose support 302 is configured to include a connection 308, which is configured to attach or connect support arm 304 to nose support 302. Nose support 302 can be configured to be formed of a semi-rigid or rigid material. In addition, nose support 302 can be configured to include a pad (not shown) to provide cushioning and compliance with nose 26. Nose support 302 can be shaped in an arc that approximately matches the curvature of nose 26.

Support arm 304 can be configured to be rigidly attached to nose support 302 by connection 308. Alternatively, connection 308 can be configured to swivel or pivot to permit a user to position support arm 304 in an orientation that assists the user in keeping nose support 302 securely in contact with nose 26. Support arm 304 is rigidly attached to controller unit 310.

Temperature sensor support 306 is movably positioned in controller unit 310, which is configured to move temperature sensor support 306 in a longitudinal direction 312, and rotatably in an arc 314. Thus, the interface of control unit 310 with support arm 304 provides the ability to adjust the position of a temperature sensor 316, positioned on temperature sensor support 306, to interface with ABTT terminus 10. It should be understood that the movement of temperature sensor support 306 may be performed manually by controls located on control unit 310, or may be automatic. If the movement is automatic, such movement is guided by readings from temperature sensor 316, which is sized and dimensioned to interface with ABTT terminus 10, and which can be configured to include a convex surface to match the concave geometry of ABTT terminus 10.

Controller unit 310 is further configured to include a switch 318 to control the on and off operation of device 300, a display or other indicator 320 configured to indicate when a user locates ABTT terminus 10, and can be configured to include a transmitter (not shown) to transmit temperature signals to a separate electronic device (not shown), which can be, for example, a laptop, cell phone, tablet, or other electronic device configured to receive the transmitted temperature signals.

Figure 21:
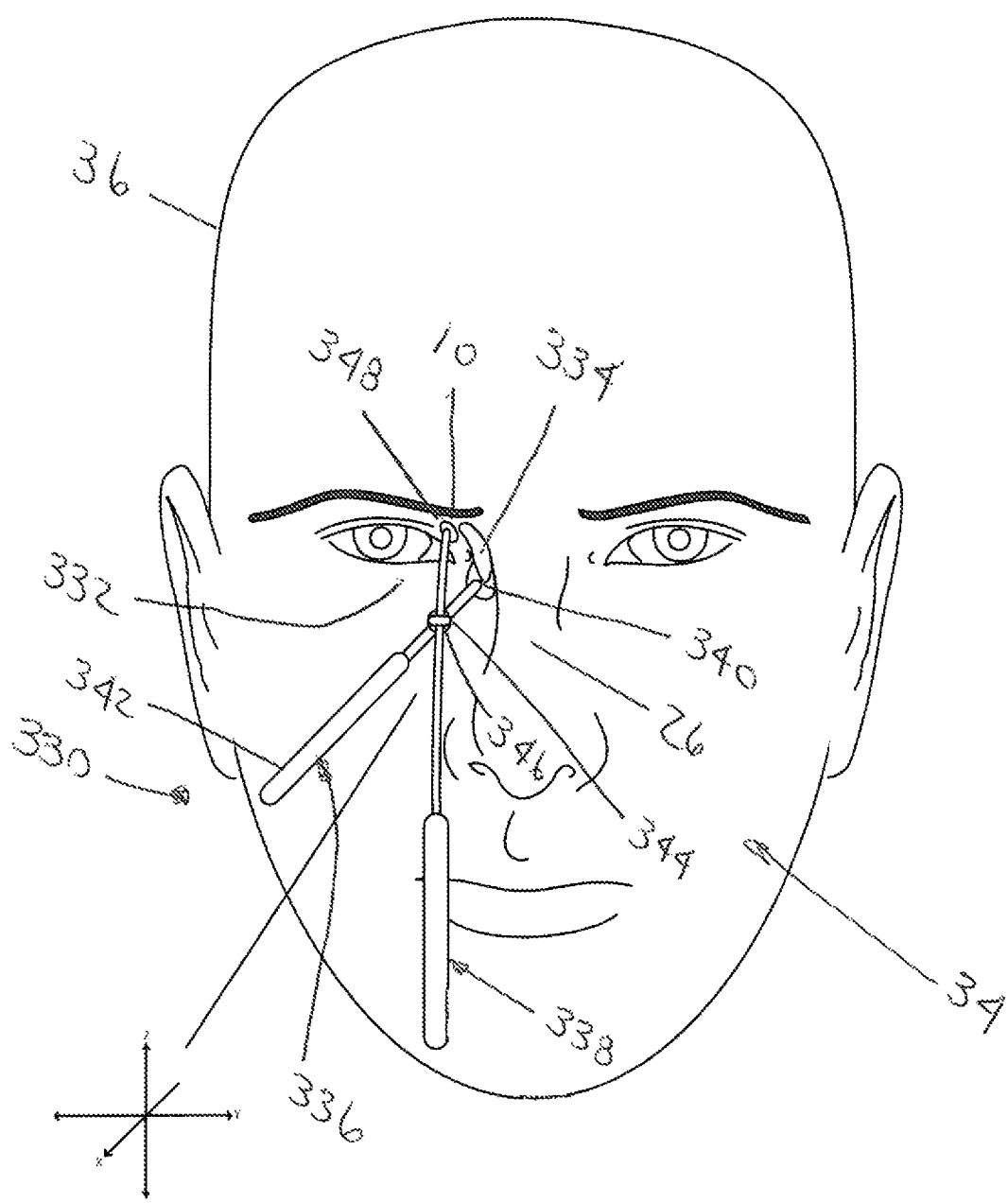
FIG. 21 is a view of a tenth device in accordance with an exemplary embodiment of the present disclosure.

FIG. 21 shows a tenth device in accordance with an exemplary embodiment of the present disclosure, indicated generally at 330. Device 330 is configured to be supported on a corner of an ocular cavity 332 adjacent to nose 26 of face 34 of subject or patient 36. As should be understood from the following description, device 330 is configured to be held in place by a user while the user positions a sensor on ABTT terminus 10.

Device 330 is configured to include a face support 334, a support arm 336, and a temperature sensor support 338. Support 334 is configured to include a connection 340, which is configured to attach or connect support arm 336 to support 334. Support 334 can be configured to be formed of a semi-rigid or rigid material that can be shaped in an arc that approximately matches the curvature of nose 26. In addition, support 334 can be configured to include a pad (not shown) to provide cushioning and compliance with ocular cavity 332 and nose 26.

Support arm 336 can be configured to be rigidly attached to support 334 by connection 340. Alternatively, connection 340 can be configured to swivel or pivot to permit a user to position support arm 336 in an orentation that assists the user in keeping support 334 securely in contact with ocular cavity 332 and nose 26. Support arm 336 is configured to include a handle 342 sized and dimensioned to permit a user to hold support arm 336 securely. Temperature sensor support 338 is connected to support arm 336 by a pivot 344, which is also configured to permit temperature sensor support 338 to move longitudinally through an eyelet 346 located in pivot 344.

Temperature sensor support 338 is configured to include a temperature sensor 348, which is sized and dimensioned to interface with ABTT terminus 10, and which can be configured to include a convex surface to match the concave geometry of ABTT terminus 10. Device 330 can be configured with the features of other embodiments disclosed herein, such as a switch to turn device 330 on and off, an indicator, and a transmitter, though such are not specifically indicated in this embodiment.

Pivot 344 is configured to both slidably and movably support temperature sensor support 338 to permit a user to move temperature sensor support 338 such that temperature sensor 348 is positionable on ABTT terminus 10, which can be located by the user as described herein.

Figure 22:
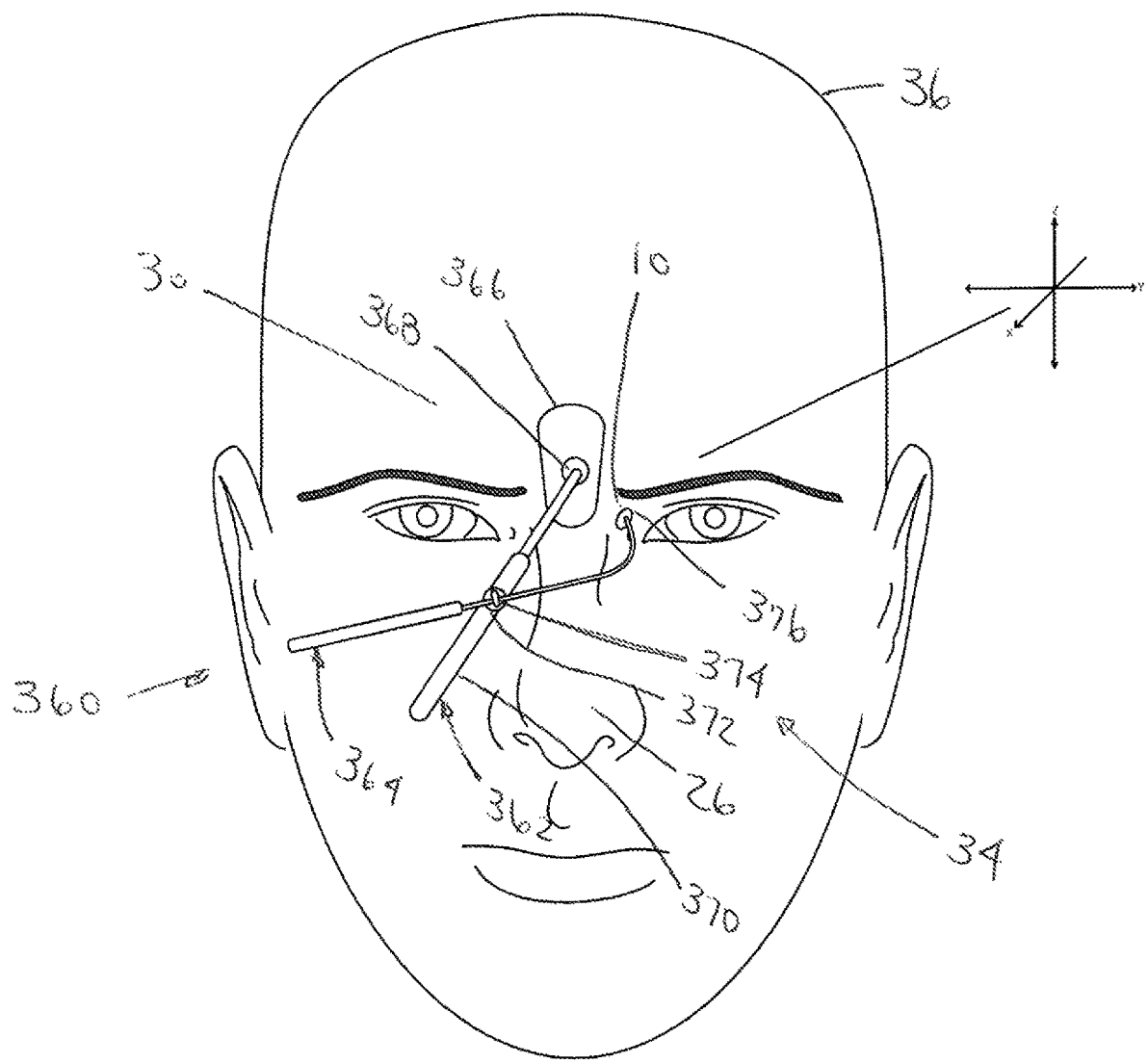
FIG. 22 is a view of an eleventh device in accordance with an exemplary embodiment of the present disclosure.

FIGS. 22-24 show an eleventh device in accordance with an exemplary embodiment of the present disclosure, indicated generally at 360. Device 360 is configured to be supported on a center of forehead 30 just above nose 26 of face 34 of subject or patient 36. As should be understood from the following description, device 360 is configured to be held in place by a user while the user positions a sensor on ABTT terminus 10.

Device 360 is configured to include a support arm 362, a temperature sensor support 364, and a face support 366. Support 366 is configured to include a connection 368, which is configured to attach or connect support arm 362 to support 366. Support 366 can be configured to be formed of a semi-rigid or rigid material that can be shaped in an arc that approximately matches the curvature of nose 26. In addition, support 366 can be configured to include a pad (not shown) to provide cushioning and compliance with forehead 30.

Support arm 362 can be configured to be rigidly attached to support 366 by connection 368. Alternatively, connection 368 can be configured to swivel or pivot to permit a user to position support arm 362 in an orientation that assists the user in keeping support 366 securely in contact with forehead 30. Support arm 362 is configured to include a handle 370 sized and dimensioned to permit a user to hold support arm 362 securely. Temperature sensor support 364 is connected to support arm 362 by a pivot 372, which is also configured to permit temperature sensor support 364 to move longitudinally through an eyelet 374 located in pivot 372.

Temperature sensor support 364 is configured to include a temperature sensor 376, which is sized and dimensioned to interface with ABTT terminus 10, and which can be configured to include a convex surface to match the concave geometry of ABTT terminus 10. As shown in FIGS. 23 and 24, device 360 can be configured with the features of other embodiments disclosed herein, such as a switch 378 to turn device 360 on and off, an indicator 380, and a transmitter 382.

Pivot 372 is configured to both slidably and movably support temperature sensor support 364 to permit a user to move temperature sensor support 364 such that temperature sensor 376 is positionable on ABTT terminus 10, which can be located by the user as described herein.

Figure 25:
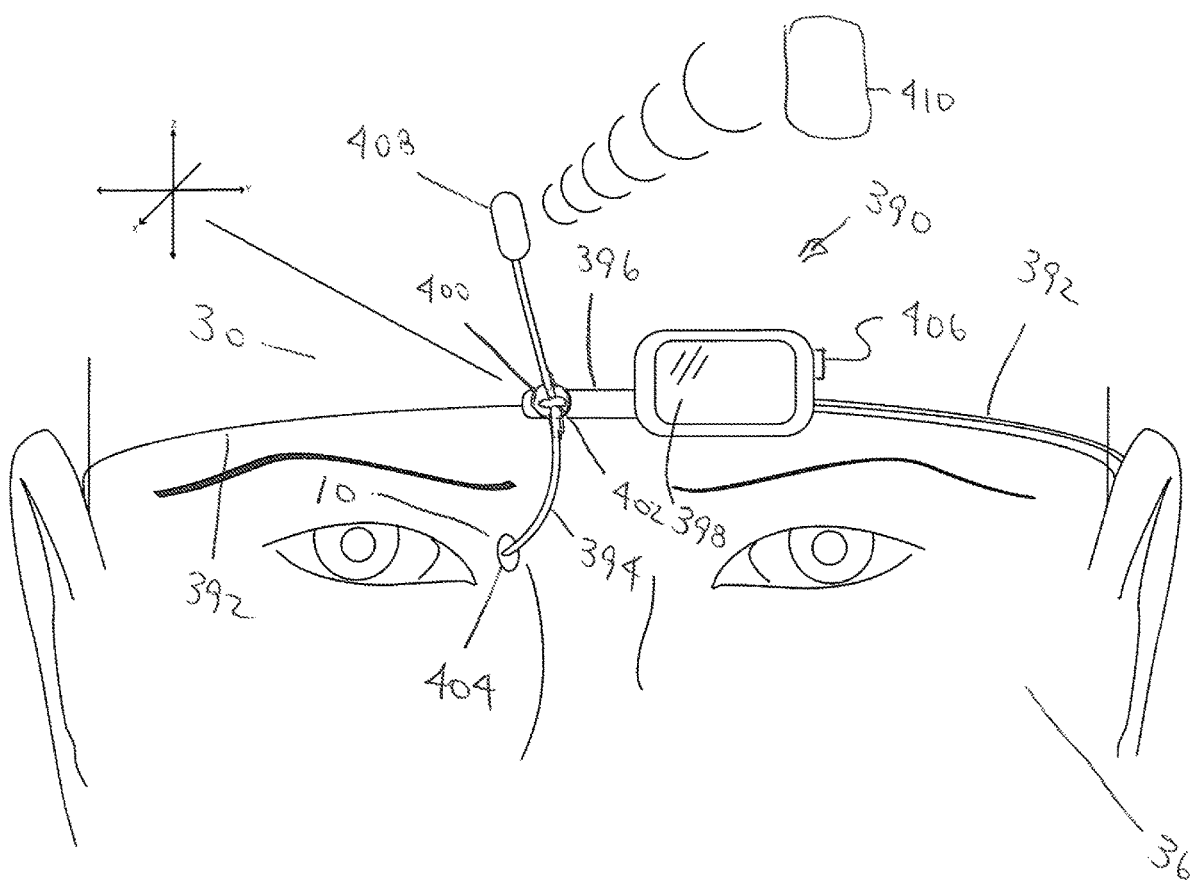
FIG. 25 is a view of a twelfth device in accordance with an exemplary embodiment of the present disclosure.

FIG. 25 shows a twelfth device in accordance with an exemplary embodiment of the present disclosure, indicated generally at 390. Device 390 is configured to be supported on forehead 30 of subject or patient 36. As should be understood from the following description, device 390 is configured to be secured on forehead 30 while a temperature sensor is moveable to be positioned on ABTT terminus 10.

Device 390 is configured to include a headband or forehead support 392, a temperature sensor support 394, a support 396, and a display or monitor 398. Monitor 398 and temperature sensor support 394 are positioned on support 396, which is positioned on headband 392. Support 396 is configured to include a pivot 400, which is configured to attach or connect temperature sensor support 394 to support 396.

Pivot 400 is configured to rotate. Furthermore, pivot 400 includes an eyelet 402. Thus, temperature sensor support 394 is configured to rotate with respect to support 396, and is longitudinally movable through eyelet 402, such that temperature sensor support 394 is movable to adjust the position of a temperature sensor 404 to be on, over, or adjacent to ABTT terminus 10.

Temperature sensor 404 is sized and dimensioned to interface with ABTT terminus 10, and which can be configured to include a convex surface to match the concave geometry of ABTT terminus 10.

Device 390 is further configured to include a switch 406 to turn device 390 on and off, and a transmitter 408. Transmitter 408 is configured to transmit information to a separate electronic device 410, such as a cell phone, tablet, laptop, watch, entertainment console, etc.

In operation, device 390 is configured to display information on monitor 398, which is readable by an operator, medical practitioner, lab technician, etc. In an alternative embodiment, device 390 is configured to display information in a flipped orientation to permit reading of the displayed information in a mirror by a patient or subject. In yet another alternative embodiment, device 390 is switchable between displaying information in a conventional format, and a flipped format for readability in a mirror.

Figure 26:
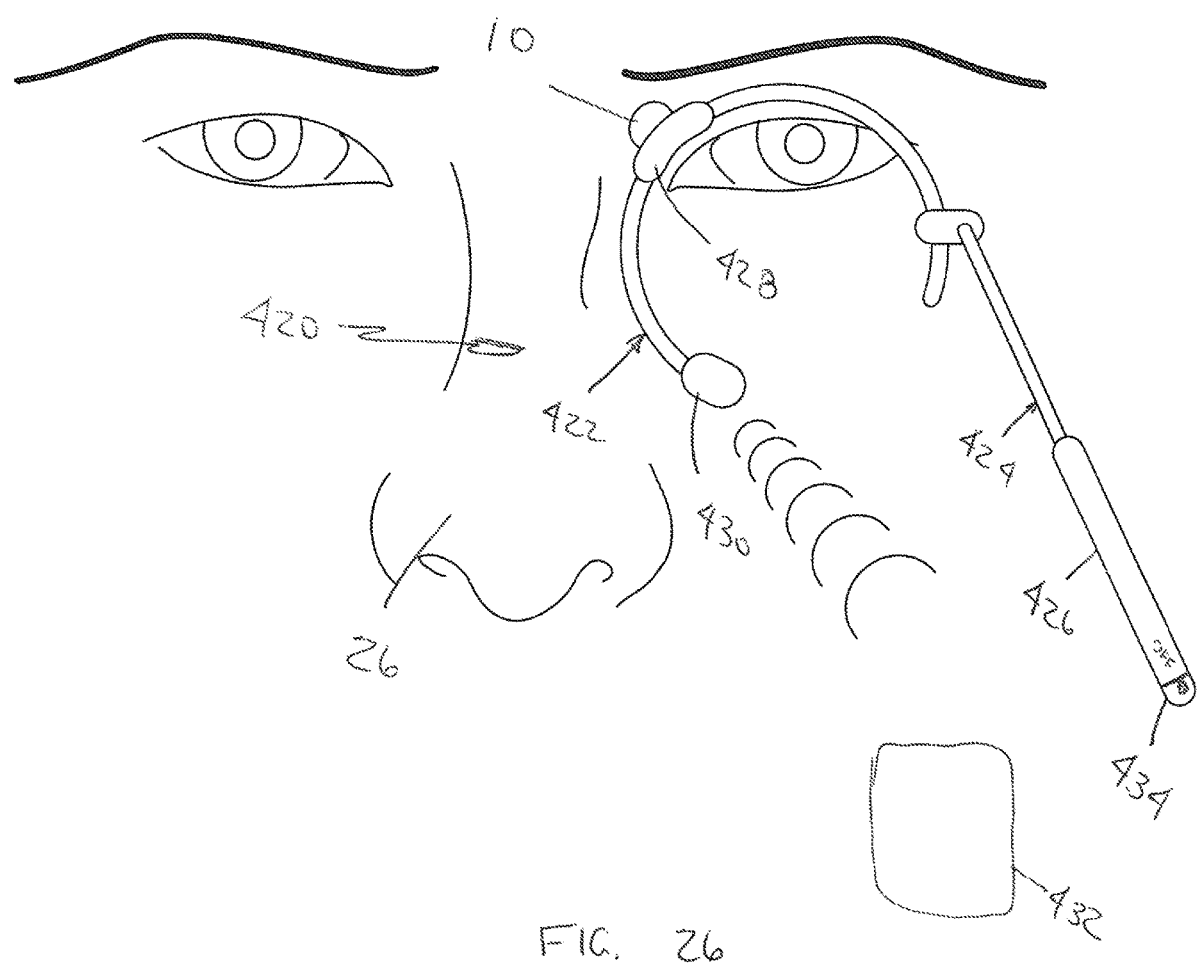
FIG. 26 is a view of a thirteenth device in accordance with an exemplary embodiment of the present disclosure.

FIG. 26 is a view of a thirteenth device in accordance with an exemplary embodiment of the present disclosure, indicated generally at 420. Device 420 is configured to include a face support ring 422 and a support arm 424. Support arm 424 is configured to include a handle 426. Support ring 422 is configured to provide support and positioning for a temperature sensor 428 and a transmitter 430, which is configured to communicate with a separate electronic device 432. Support arm 424 can also be configured to include a switch 434 for turning device 420 on and off. Device 420 is configured to be positioned in ocular cavity 332, alongside nose 26, thus properly orienting temperature sensor 428.

Figure 27:
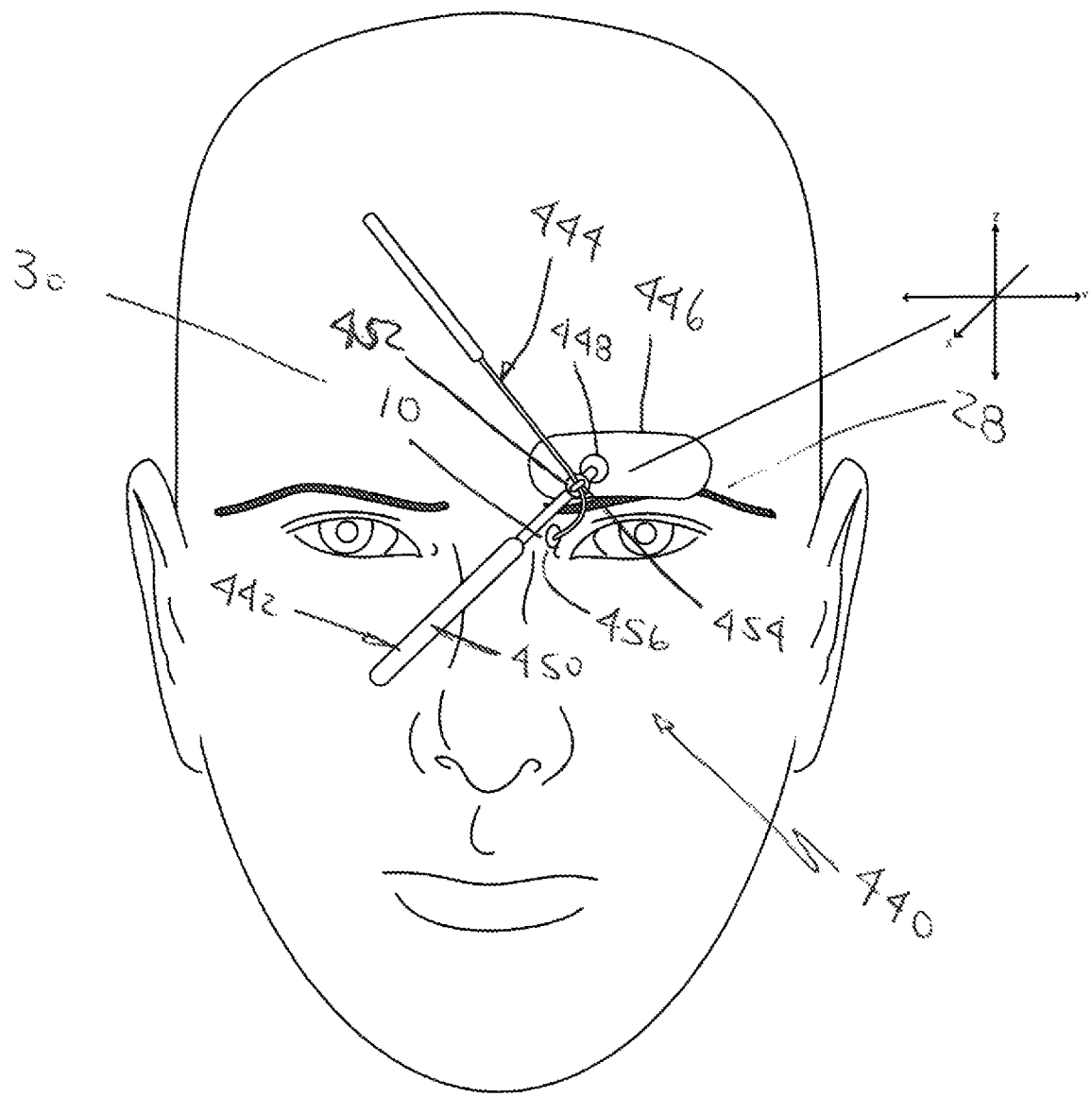
FIG. 27 is a view of a fourteenth device in accordance with an exemplary embodiment of the present disclosure.

FIGS. 27-29 show a fourteenth device in accordance with an exemplary embodiment of the present disclosure, indicated generally at 440. Device 440 is configured to be supported just above eyebrow 28 on forehead 30. As should be understood from the following description, device 440 is configured to be held in place by a user while the user positions a sensor on ABTT terminus 10.

Device 440 is configured to include a support arm 442, a temperature sensor support 444, and a forehead or face support 446. Support 446 is configured to include a connection 448, which is configured to attach or connect support arm 442 to support 446. Support 446 can be configured to include a pad (not shown) to provide cushioning and compliance with forehead 30.

Support arm 442 can be configured to be rigidly attached to support 446 by connection 448. Alternatively, connection 448 can be configured to swivel or pivot to permit a user to position support arm 442 in an orientation that assists the user in keeping support 442 securely in contact with forehead 30. Support arm 442 is configured to include a handle 450 sized and dimensioned to permit a user to hold support arm 442 securely. Temperature sensor support 444 is connected to support arm 442 by a pivot 452, which is also configured to permit temperature sensor support 444 to move longitudinally through an eyelet 454 located in pivot 452.

Temperature sensor support 444 is configured to include a temperature sensor 456, which is sized and dimensioned to interface with ABTT terminus 10, and which can be configured to include a convex surface to match the concave geometry of ABTT terminus 10. As shown in FIGS. 28 and 29, device 440 can be configured with a control unit 458, which is configured to include a switch 460 to turn device 440 on and off, an indicator or display 462, and a transmitter 464 that is configured to communicate with a separate electronic device 466.

Pivot 452 is configured to both slidably and rotatably support temperature sensor support 444 to permit a user to move temperature sensor support 444 such that temperature sensor 456 is positioned on ABTT terminus 10, which can be located by the user as described herein.

FIGS. 30 and 31 show a fifteenth device in accordance with an exemplary embodiment of the present disclosure, indicated generally at 470. Device 470 is configured to be supported just above eyebrow 28 on forehead 30. As should be understood from the following description, device 470 is configured to be held in place by a user while the user positions a sensor on ABTT terminus 10.

Device 470 is configured to include a support arm 472, a temperature sensor support 474, and a face support 476. Support 476 is configured to include a connection 478, which is configured to attach or connect support arm 472 to support 476. Support 476 can be configured to include a pad (not shown) to provide cushioning and compliance with forehead 30.

Support arm 472 can be configured to be rigidly attached to support 476 by connection 478. Alternatively, connection 478 can be configured to swivel or pivot to permit a user to position support arm 472 in an orientation that assists the user in keeping support 472 securely in contact with forehead 30. Support arm 472 is configured to include a handle 480 sized and dimensioned to permit a user to hold support arm 472 securely. Temperature sensor support 474 is connected to support arm 472 by a pivot 482, which is also configured to permit temperature sensor support 474 to move longitudinally through an eyelet 484 located in pivot 482.

Temperature sensor support 484 is configured to include a temperature sensor 486, which is sized and dimensioned to interface with ABTT terminus 10, and which can be configured to include a convex surface to match the concave geometry of ABTT terminus 10. Device 470 can be configured with a control unit 488, which is configured to include a switch 490 to turn device 470 on and off, an indicator 492, and a transmitter 494 that is configured to communicate with a separate electronic device 466.

Pivot 482 is configured to both slidably and rotatably support temperature sensor support 474 to permit a user to move temperature sensor support 474 such that temperature sensor 486 is positioned on ABTT terminus 10, which can be located by the user using procedures described herein.

FIG. 32 shows a sixteenth device in accordance with an exemplary embodiment of the present disclosure, indicated generally at 500. Device 500 is configured to be supported at least partially on eye 32. As should be understood from the following description, device 500 is configured to be held in place by a user while the user positions a sensor on ABTT terminus 10.

Device 500 is configured to include a temperature sensor support 502, and a face support 504. Support 504 is configured to include a connection 506, which is configured to attach or connect temperature sensor support 502 to support 504. Support 504 is configured to include a temperature sensor 508, which is sized and dimensioned to interface with ABTT terminus 10, and which can be configured to include a convex surface to match the concave geometry of ABTT terminus 10.

Temperature sensor support 502 can be configured to be rigidly attached to support 504 by connection 506. Alternatively, connection 506 can be configured to swivel or pivot to permit a user to position temperature sensor support 502 in an orientation that assists the user in keeping support 504 securely in contact with ABTT terminus 10 and with a portion of eye 32. Temperature sensor support 502 is configured to include a handle 510 sized and dimensioned to permit a user to hold temperature sensor support 502 securely.

Device 500 is configured with a control unit 512, which is configured to include a switch 514 to turn device 500 on and off, an indicator or display 516, and a transmitter 518 that is configured to communicate with a separate electronic device 520. Temperature sensor support 502 can also be configured to include an indicator 522 that provides an indicator of when a user locates ABTT terminus 10.

Figure 33:
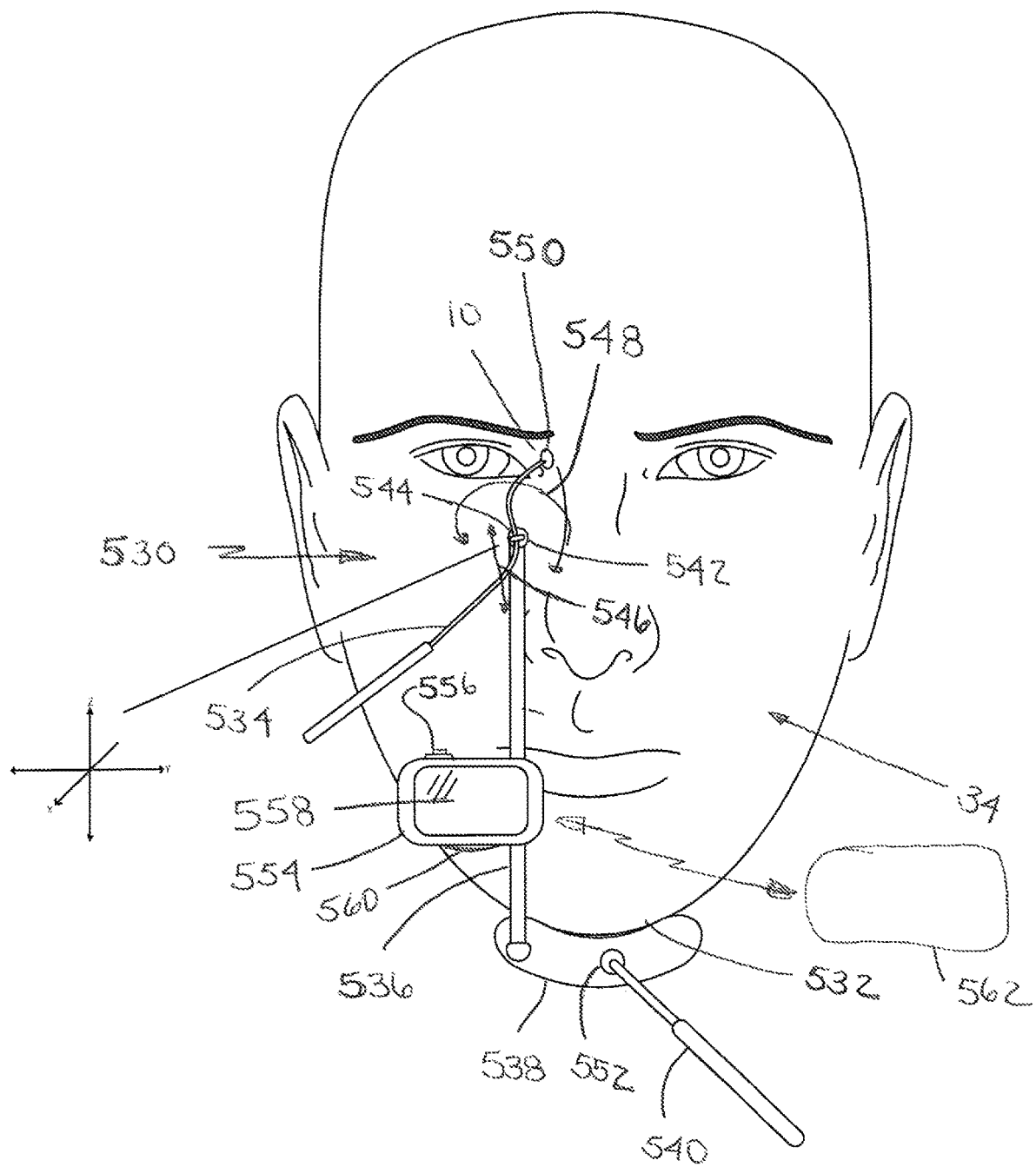
FIG. 33 is a view of a seventeenth device in accordance with an exemplary embodiment of the present disclosure.

FIG. 33 shows a seventeenth device in accordance with an exemplary embodiment of the present disclosure, indicated generally at 530. Device 530 is configured to be supported at least partially on a chin 532 of face 34. As should be understood from the following description, device 530 is configured to be held in place by a user while the user positions a sensor on ABTT terminus 10.

Device 530 is configured to include a temperature sensor support 534, which is configured to include a temperature sensor 550, a central support 536, a face or chin support 538, and a securing handle 540. Temperature sensor 550 is sized and dimensioned to interface with ABTT terminus 10, and which can be configured to include a convex surface to match the concave geometry of ABTT terminus 10. Chin support 538 is rigidly connected to central support 536. Temperature sensor support 534 is rotatably and slidably connected to central support 536. And securing handle 540 can be rigidly or pivotally connected to chin support 538.

Central support 536 is configured to include a pivot 542, which includes an eyelet 544. Temperature sensor support 534 is slidably positioned in eyelet 544, and the slidable arrangement is configured to provide temperature sensor support 534 with the capability of sliding longitudinally in a direction 546. Pivot 542 is configured to rotate in an arc 548, which provides temperature sensor support 534 with the capability to rotate in arc 548. Since temperature sensor support 534 is configured with the capability to rotate in arc 548 and to slide in longitudinal direction 546, temperature sensor support 534 is configured to move by the action of a user to adjust the position of temperature sensor 550 to be located at the position of ABTT terminus 10.

Chin support 538 is configured to include a connection 552, which is configured to attach or connect securing handle 540 to chin support 538. Securing handle 540 can be configured to be rigidly attached to chin support 538 by connection 552. Alternatively, connection 552 can be configured to swivel or pivot to permit a user to position securing handle 540 in an orientation that assists the user in keeping chin support 538 securely in contact with chin 532.

Device 530 is configured to include a control unit 554, which is configured to include a switch 556 to turn device 530 on and off, an indicator or display 558, and a transmitter 560 that is configured to communicate with a separate electronic device 562, which can be a tablet, cell phone, laptop, PDA, entertainment console, watch, medical control console, etc.

FIGS. 34 and 35 show an eighteenth device in accordance with an exemplary embodiment of the present disclosure, indicated generally at 570. Device 570 is configured to be supported on face 34 of subject or patient 36. More specifically, device 570 can be configured as a frame or eyeglass frame 572. Device 570 further includes a clip-on or attachable temperature sensor assembly 574.

Temperature sensor assembly 574 includes a connection assembly 576, a temperature sensor support 578, and a handle or lever 580. Temperature sensor support 578 is configured to include a temperature sensor 582. Connection assembly 576 can be configured similar to pivot 482, and thus temperature sensor support 578 can be configured to have rotational and longitudinal movement such that temperature sensor 582 can be positioned through the movement of temperature sensor support 578 to be positioned on ABTT terminus 10. Alternatively, temperature sensor support 578 can be configured to be flexible to permit adjustment of temperature sensor support 578 to position temperature sensor 582 on ABTT terminus 10.

Temperature sensor assembly 574 is further configured to include a switch 584 to turn device 570 on and off, an indicator or light 586, and a transmitter 588 that is configured to communicate with a separate electronic device 590, which can be a tablet, cell phone, laptop, PDA, entertainment console, watch, medical control console, etc.

Figure 36:
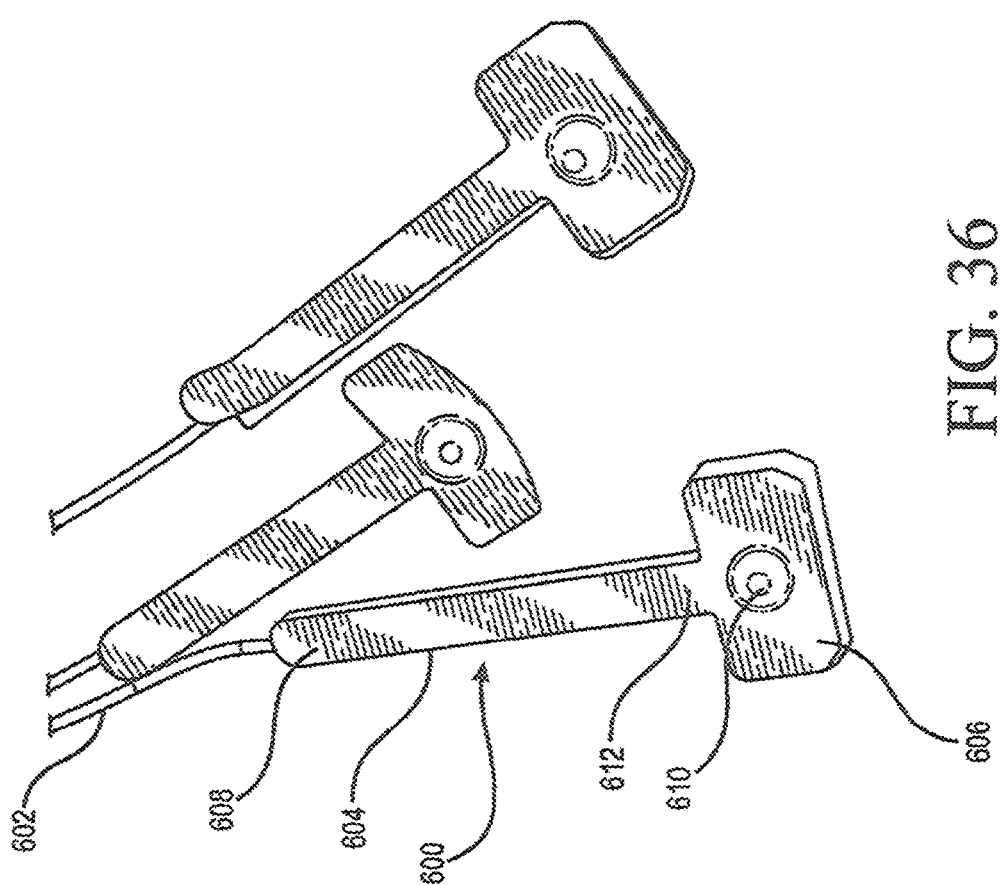
FIG. 36 is a perspective view of a nineteenth device in accordance with an exemplary embodiment of the present disclosure.

FIG. 36 is a view of a nineteenth device in accordance with an exemplary embodiment of the present disclosure, indicated generally at 600. Device 600 is configured to include a wire 602, an arm 604, and a head 606. Arm 604 and head 606 include a protective layer 608, which covers an adhesive layer. Head 606 is configured to include a temperature sensor 610. Device 600 can be ear supported by wire 602, with the adhesive layer securing arm 604 to a subject or patient's forehead. Head portion 606 is configured to be bendable in area 612 to permit head 606 and sensor 610 to be positioned under an eyebrow on ABTT terminus 10. The width of head 606 is such that heat 606 can be partially anchored on a patient's nose as well as a portion of an eyelid adjacent ABTT terminus 10.

While various embodiments of the disclosure have been shown and described, it is understood that these embodiments are not limited thereto. The embodiments can be changed, modified, and further applied by those skilled in the art. Therefore, these embodiments are not limited to the detail shown and described previously, but also include all such changes and modifications.

I claim:

1. A device configured to position a sensor on a human head, the device comprising:
a face support ring, the face support ring including a first end and a second end;
a transmitter positioned on the face support ring at the first end;
a support arm positioned on the face support ring closer to the second end than to the first end; and
a temperature sensor positioned directly on the face support ring at a location that is between the transmitter and the support arm.

2. The device according to claim 1, wherein the temperature sensor is configured to receive temperature signals of a subject.

3. The device according to claim 2, wherein the transmitter is configured to transmit the temperature signals of the subject to a separate electronic device that is configured to receive the transmitted temperature signals.

4. The device according to claim 3, wherein the separate electronic device is one of a lap top, a cell phone, a computer, a tablet, and a watch.

5. The device according to claim 1, wherein the transmitter is a transceiver configured to transmit and receive signals.

6. The device according to claim 1, further comprising a handle directly attached to the support arm.

7. The device according to claim 6, wherein the handle is directly attached to a second end of the support arm opposite from a first end of the support arm that is positioned to the face support ring.

8. The device according to claim 6, wherein the handle and the support arm are aligned in a straight line.

9. The device according to claim 6, wherein the handle includes a switch for turning the device off and on.

10. The device according to claim 6, wherein the handle has a diameter larger than a diameter of the support arm.

11. The device according to claim 1, wherein the device is configured to allow for the temperature sensor to be positionable on an Abreu brain thermal tunnel (ABTT) terminus to measure a temperature of the ABTT.

12. The device according to claim 1, wherein the face support ring has an annular shape.

13. The device according to claim 12, wherein the face support ring has a diameter that allows for the device to be positioned in an ocular cavity along side a nose of a subject.

14. The device according to claim 1, wherein there is a gap between the first end and the second end of the face support ring.

15. The device according to claim 3, wherein the temperature signals from the temperature sensor are transmitted continuously from the transmitter to the separate electronic device.

16. The device according to claim 3, wherein the temperature signals from the temperature sensor are transmitted in a burst by the transmitter to the separate electronic device.

17. The device according to claim 6, wherein the handle further includes an indicator configured to indicate when an Abreu brain thermal tunnel (ABTT) terminus is located.

18. The device according to claim 17, wherein the indicator is a light that is configured to turn on when the ABTT terminus is located.

19. The device according to claim 7, wherein the face support ring has an annular shape.

* * * * *